United States Patent
Forth et al.

(10) Patent No.: US 8,207,191 B2
(45) Date of Patent: Jun. 26, 2012

(54) PROCESS, SALTS, COMPOSITION AND USE

(75) Inventors: Michael Anthony Forth, Tonbridge (GB); Susan ShuMei Hu Kopelman, King of Prussia, PA (US); Francis Xavier Muller, King of Prussia, PA (US); Francis Dominic Sanderson, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 12/977,127

(22) Filed: Dec. 23, 2010

(65) Prior Publication Data

US 2011/0144151 A1   Jun. 16, 2011

Related U.S. Application Data

(62) Division of application No. 10/570,410, filed as application No. PCT/US2004/028159 on Aug. 30, 2004, now Pat. No. 7,875,630.

(60) Provisional application No. 60/499,781, filed on Sep. 3, 2003.

(51) Int. Cl.
   *A61K 31/44* (2006.01)
   *C07D 451/02* (2006.01)
(52) U.S. Cl. .................. 514/304; 546/132; 546/124
(58) Field of Classification Search .................. 514/305, 514/299, 304; 546/112, 133, 132, 124
See application file for complete search history.

(56) References Cited

U.S. PATENT DOCUMENTS

| 4,278,674 A | 7/1981 | Egger et al. |
| 4,428,953 A | 1/1984 | Berner et al. |
| 6,281,226 B1 | 8/2001 | Berry et al. |
| 6,784,193 B1 | 8/2004 | Ascher et al. |
| RE39,128 E | 6/2006 | Berry et al. |
| 2005/0215637 A1 | 9/2005 | Ascher et al. |
| 2005/0250811 A1 | 11/2005 | Berner et al. |
| 2006/0276503 A1 | 12/2006 | Breen et al. |

FOREIGN PATENT DOCUMENTS

| WO | WO 01/37828 A1 | 5/2001 |
| WO | WO 2006/092334 | 9/2006 |
| WO | WO 2006/104667 | 10/2006 |

OTHER PUBLICATIONS

Suzanne F. Bradley, M.D., Semin Respir Crit Care Med. 2005; 26(6):643-649.
Gennaro Alfonso, Remington's Pharm Sciences, 1990, Mack Publishing Co., 18$^{th}$ ed., pp. 1310.
Abst. of the Interscience Conf. on Antimicrobial Agents and Chemother., vol. 39, p. 337 & 39th Interscience Conf. on Antimicrobial Agents and Chemother., Sep. 26-29, 1999.
New Experimental Chemistry Lecture 14—Synthesis and Reaction of Organic Compounds III, Maurzen Co., Ltd., 1978, p. 1705 (article with translated section).

*Primary Examiner* — Tayloir Victor Oh
(74) *Attorney, Agent, or Firm* — Dara L. Dinner; Theodore Furman

(57) ABSTRACT

The present invention provides a novel process for preparing pleuromutilin derivatives, novel salts of mutilin 14-(exo-8-methyl-8-azabicyclo[3.2.1]oct-3-ylsulfanyl)-acetate or solvates thereof, novel pharmaceutical compositions or formulations for topical administration comprising mutilin 14-(exo-8-methyl-8-azabicyclo[3.2.1]oct-3-ylsulfanyl)-acetate or a pharmaceutically acceptable salt or solvate thereof and their use in medical therapy, particularly antibacterial therapy.

24 Claims, 15 Drawing Sheets

PROCESS, SALTS, COMPOSITION AND USE

RELATED INFORMATION

This application is a divisional of U.S. Ser. No. 10/570,410 (allowed) filed Mar. 3, 2006 now U.S. Pat. No. 7,875,630 which is the §371 national stage entry of PCT/US2004/028159, filed 30 Aug. 2004 which claims the benefit of U.S. Ser. No. 60/499,781 filed 3 Sep. 2003.

FIELD OF THE INVENTION

The present invention relates to a novel process for preparing pleuromutilin derivatives, to novel salts of mutilin 14-(exo-8-methyl-8-azabicyclo[3.2.1]oct-3-ylsulfanyl)-acetate or solvates thereof, to novel pharmaceutical compositions or formulations for topical administration comprising mutilin 14-(exo-8-methyl-8-azabicyclo[3.2.1]oct-3-ylsulfanyl)-acetate or a pharmaceutically acceptable salt or solvate thereof and to their use in medical therapy, particularly antibacterial therapy.

BACKGROUND OF THE INVENTION

International patent application no. WO99/21855 (SmithKline Beecham plc and SmithKline Beecham Corporation) describes pleuromutilin derivatives of general formula (A) or (B):

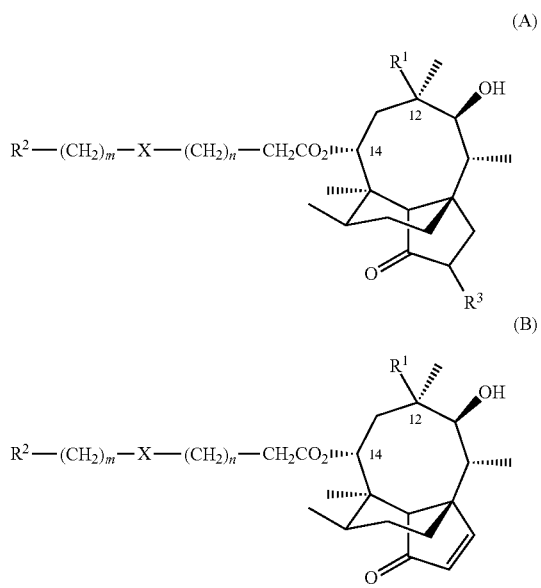

in which:
each of n and m is independently 0, 1 or 2;
X is selected from —O—, —S—, —S(O)—, —SO$_2$—, —CO.O—, —NH—, —CONH—, —NHCONH— and a bond;
$R^1$ is vinyl or ethyl;
$R^2$ is a non-aromatic monocyclic or bicyclic group containing one or two basic nitrogen atoms and attached through a ring carbon atom;
$R^3$ is H or OH; or
the moiety $R^2(CH_2)_mX(CH_2)_nCH_2COO$ at position 14 of (IA) or (IB) is replaced by $R^aR^bC$=CHCOO in which one of $R^a$ and $R^b$ is hydrogen and the other is $R^2$ or $R^a$ and $R^b$ together form $R^2$, or
a pharmaceutically acceptable salt thereof.

One of the compounds described in WO99/21855 is the compound of formula (C), mutilin 14-(exo-8-methyl-8-azabicyclo[3.2.1]oct-3-ylsulfanyl)-acetate:

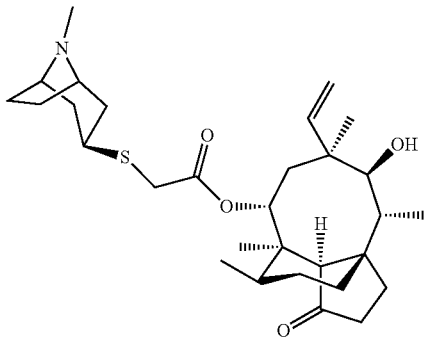

Two processes for the preparation of this compound are described in Examples 50 and 58 of WO99/21855. In the first process, mutilin 14-methanesulfonyloxyacetate is added to endo-8-methyl-8-azabicyclo[3.2.1]octan-3-thiol in the presence of potassium t-butoxide in ethanol, to give the product in a yield of 17% based on the amount of pleuromutilin derived starting material, after purification. The thiol was prepared from the corresponding hydroxy compound via the corresponding thioacetate. In the second process, the methane sulfonate leaving group is located on the methyl-8-azabicyclo [3.2.1]octyl component which is added to 22-deoxy-22-sulfanylpleuromutilin in the presence of sodium methoxide, to give the product in a yield of 27% based on the amount of pleuromutilin derived starting material, after purification.

SUMMARY OF THE INVENTION

The present invention provides a novel process for preparing pleuromutilin derivatives, novel salts of mutilin 14-(exo-8-methyl-8-azabicyclo[3.2.1]oct-3-ylsulfanyl)-acetate or solvates thereof, novel pharmaceutical compositions or formulations for topical administration comprising mutilin 14-(exo-8-methyl-8-azabicyclo[3.2.1]oct-3-ylsulfanyl)-acetate or a pharmaceutically acceptable salt or solvate thereof and their use in medical therapy, particularly antibacterial therapy.

DETAILED DESCRIPTION OF THE INVENTION

Figure 1:
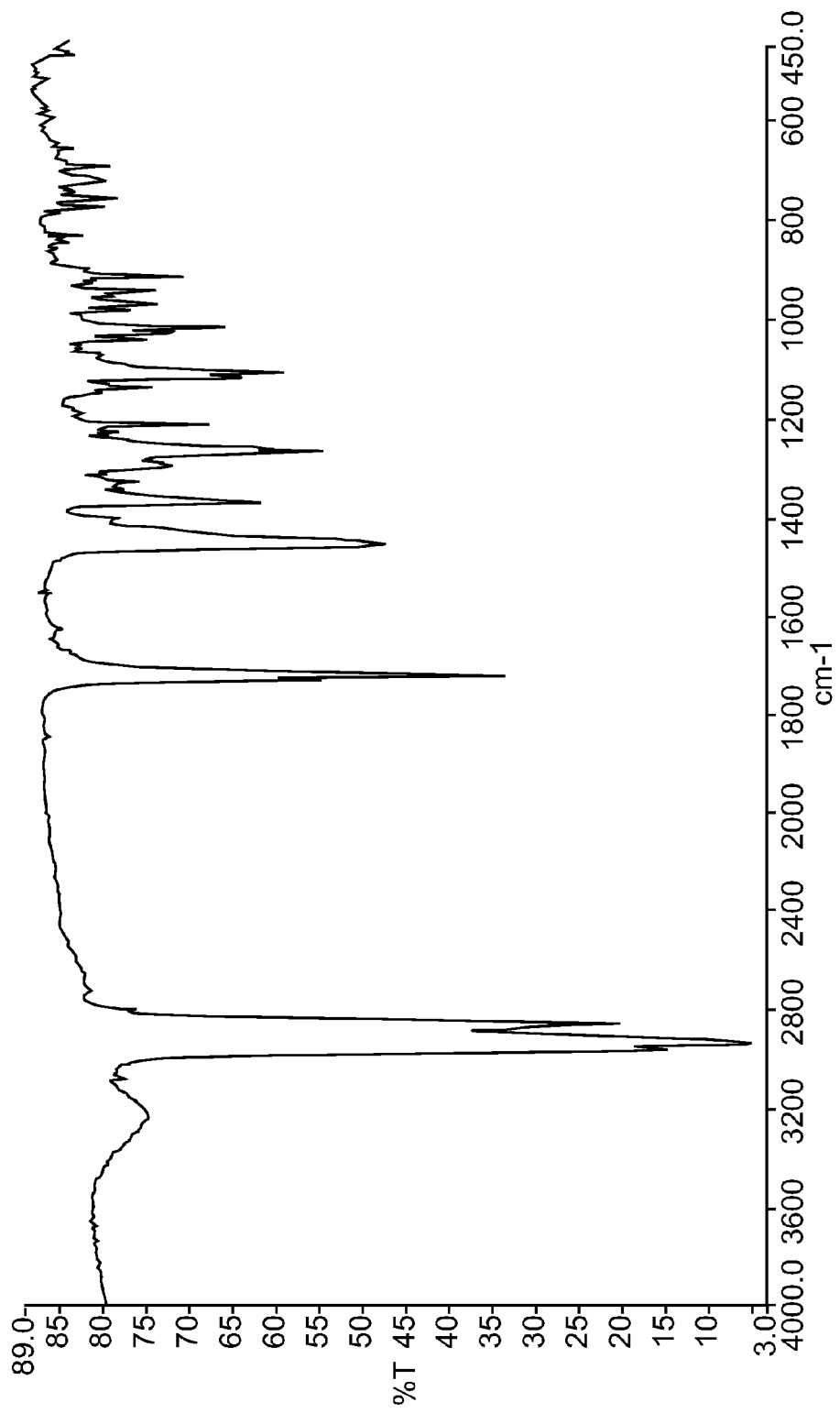
FIG. 1 is an infra-red spectrum of crystalline mutilin 14-(exo-8-methyl-8-azabicyclo[3.2.1]oct-3-ylsulfanyl)-acetate measured by ATR (attenuated total reflectance).

According to a first aspect of the present invention we have found a novel process for preparing pleuromutilin derivatives using a thiol in a phase transfer catalysis system. The phase transfer catalysis process provides a more efficient synthesis, with improved yield, and avoids a chromatography step to purify the reaction product.

Thus in one embodiment the present invention provides a process for preparing a compound of formula (IA) or (IB):

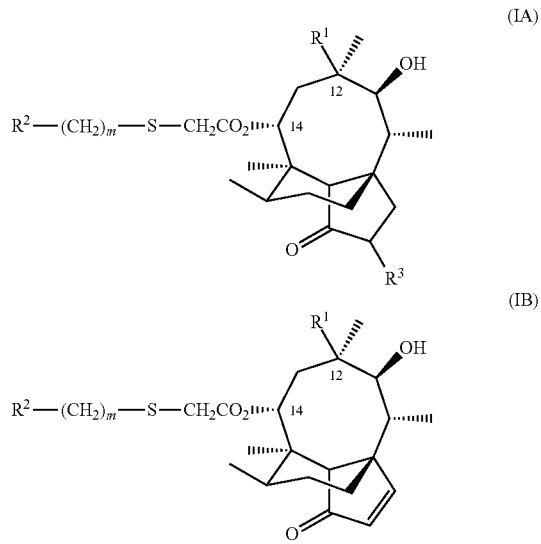

in which:
m is 0, 1 or 2;
$R^1$ is vinyl or ethyl;
$R^2$ is an optionally substituted non-aromatic monocyclic or bicyclic group containing one or two basic nitrogen atoms and attached through a ring carbon atom;
$R^3$ is H or OH; or
a pharmaceutically acceptable derivative thereof;
which process comprises reacting a compound of formula (IIA) or (IIB):

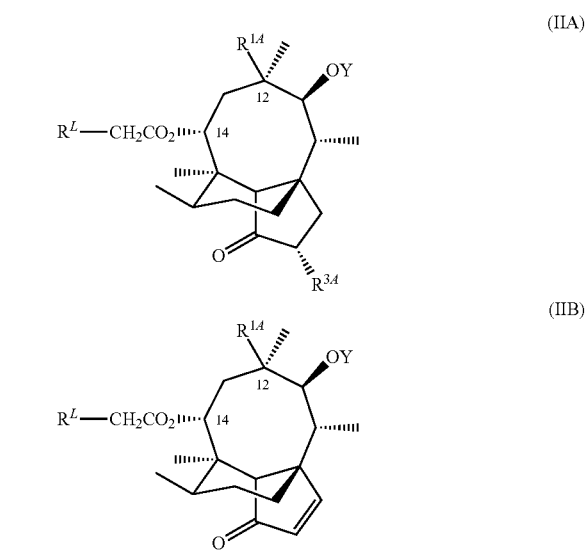

in which:
Y is hydrogen or a hydroxy protecting group;
$R^{1A}$ and $R^{3A}$ are $R^1$ and $R^3$ as defined for formulae (IA) and (IB) or groups convertible to
$R^1$ and $R^3$; and
$R^L$ is a leaving group, OH or $NH_2$;
with a thiol compound of formula (III):

$$R^{2A}-(CH_2)_m-SH \qquad (III)$$

in which:
$R^{2A}$ is $R^2$ as defined for formulae (IA) and (IB) or a group convertible to $R^2$, and
m is as defined for formulae (IA) and (IB);
in a phase transfer catalysis system;
and thereafter, where required or desired,
converting Y to hydrogen,
converting an $R^{1A}$, $R^{2A}$ or $R^{3A}$ group to an $R^1$, $R^2$ or $R^3$ group, and/or converting one $R^1$, $R^2$ or $R^3$ group to another $R^1$, $R^2$ or $R^3$ group.

Preferably, m is 0 or 1. In particular, m is 0.
Preferably, $R^1$ and $R^{1A}$ are vinyl.
Preferably, $R^{2A}$ is $R^2$. When $R^2$ is monocyclic, it typically contains from 4 to 8 ring atoms, and, when bicyclic, it typically contains from 5 to 10 ring atoms in each ring, and is optionally substituted by up to 3 substituents. Suitable substituents include alkyl, alkyloxy, alkenyl and alkenyloxy, each of which may be carried by either a bridgehead or a non-bridgehead atom. In addition, the or each nitrogen atom may be substituted by oxygen, to form an N-oxide, or by mono- or dialkyl, in which case it will be appreciated that a quaternary cation can be formed. The counterion may be a halide ion such as chloride or bromide, preferably chloride. The aza ring system additionally may contain one or more double bonds.

Representative bicyclic and monocyclic groups for $R^2$ include piperidinyl, pyrrolidyl, quinuclidinyl (azabicyclo[2.2.2]octyl), azabicyclo[2.2.1]heptyl, azabicyclo[4.3.0]nonyl, azabicyclo[3.2.1]octyl, azabicyclo[3.3.0]octyl, azabicyclo[3.2.1]octenyl, azabicyclo[3.3.1]nonyl and azabicyclo[4.4.0]decyl, all of which may be substituted or unsubstituted.

Preferably, $R^2$ is a bicyclic group. More preferably, $R^2$ is azabicyclo[3.2.1]octyl optionally substituted by alkyl, in particular exo-8-methyl-8-azabicyclo[3.2.1]oct-3-yl.

Preferably, $R^3$ and $R^{3,4}$ are hydrogen.

Preferably, $R^L$ is a leaving group. Examples of suitable leaving groups include 4-$CH_3C_6H_4SO_2O$ (tosylate), $CH_3SO_2O$ (mesylate), $F_3CSO_2O$, I, Br and Cl. Preferably, the leaving group is $CH_3SO_2O$.

When used herein, the term "pharmaceutically acceptable" means a compound which is suitable for pharmaceutical use. Salts and solvates of the compounds prepared according to the process of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

When used herein, the term "pharmaceutically acceptable derivative", means any pharmaceutically acceptable salt, solvate, or prodrug e.g. ester, of a compound, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters, especially salts.

The compounds prepared according to the process of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent.

Salts of the compounds prepared according to the process of the present invention may, for example, comprise acid addition salts resulting from reaction of an acid with a basic nitrogen atom present in a compound of formula (IA) or (IB). Salts encompassed within the term "pharmaceutically acceptable salts" refer to non-toxic salts of the compounds of this invention. Suitable addition salts are formed from acids which form non-toxic salts and examples include acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, dihydrochloride, edetate, edisylate, estolate, esylate, ethanedisulfonate, ethanesulfonate, formate, fumarate, gluceptate, gluconate, glutamate, glycollate, glycollylarsanilate, hexylresorcinate, hydrabamine, hydrobromide, hydrochloride, hydrofumarate, hydrogen phosphate, hydroiodide, hydromaleate, hydrosuccinate, hydroxynaphthoate, isethionate, itaconate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, oxaloacetate, pamoate (embonate), palmate, palmitate, pantothenate, phosphate/diphosphate, piruvate, polygalacturonate, propionate, saccharate, salicylate, stearate, subacetate, succinate, sulfate, tannate, tartrate, teoclate, tosylate, triethiodide, trifluoroacetate and valerate.

Pharmaceutically acceptable base salts include ammonium salts such as a trimethylammonium salt, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Compounds prepared according to the invention having both a basic and acidic centre (carboxy substituent) may be in the form of zwitterions, acid-addition salt of the basic centre or alkali metal salts (of the carboxy group).

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. This invention includes within its scope stoichiometric hydrates as well as compounds containing variable amounts of water.

When used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed.; Bioreversible Carriers in Drug Design, American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds prepared according to the invention wherein hydroxy or amine groups are bonded to any group that, when administered to a patient, cleaves to form the hydroxy or amine groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

When used herein, the term "non-aromatic" refers to groups which are saturated or unsaturated but excludes aromatic groups such as pyridine or quinoline.

Alkyl groups referred to herein (individually or as part of another group) include straight and branched groups containing from one to six carbon atoms i.e. $C_{1-6}$alkyl. Examples of such groups include, but are not limited to methyl, ethyl, propyl, isopropyl, n-butyl, isobutyl, tert-butyl, pentyl and hexyl. The alkyl groups are optionally substituted by one or more groups selected from the group consisting of aryl, heterocyclyl, $(C_{1-6})$alkoxy, $(C_{1-6})$alkylthio, aryl$(C_{1-6})$alkoxy, aryl$(C_{1-6})$alkylthio, amino, mono- or di-$(C_{1-6})$alkylamino, cycloalkyl, cycloalkenyl, carboxy and esters thereof, amides of carboxy, ureido, carbamimidoyl (amidino), guanidino, alkylsulfonyl, aminosulfonyl, $(C_{1-6})$acyloxy, $(C_{1-6})$acylamino, azido, hydroxy and halogen.

Alkenyl groups referred to herein (individually or as part of another group) include straight and branched groups containing from two to six carbon atoms i.e. $C_{2-6}$alkenyl. Examples of such groups include, but are not limited to, vinyl (ethenyl), propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl. The alkenyl groups are optionally substituted by one or more groups selected from the group consisting of aryl, heterocyclyl, $(C_{1-6})$alkoxy, $(C_{1-6})$alkylthio, aryl$(C_{1-6})$alkoxy, aryl$(C_{1-6})$alkylthio, amino, mono- or di-$(C_{1-6})$alkylamino, cycloalkyl, cycloalkenyl, carboxy and esters thereof, amides of carboxy, ureido, carbamimidoyl (amidino), guanidino, alkylsulfonyl, aminosulfonyl, $(C_{1-6})$acyloxy, $(C_{1-6})$acylamino, azido, hydroxy and halogen.

Alkyloxy, alkoxy and alkenyloxy groups referred to herein refer to the alkyl and alkenyl groups as hereinbefore defined attached to oxygen.

Cycloalkyl and cycloalkenyl groups referred to herein include groups having from three to eight ring carbon atoms. For example, $C_{3-7}$cycloalkyl means a saturated ring containing at least three, and at most seven, ring carbon atoms and $C_{3-7}$cycloalkenyl means a non-aromatic, unsaturated ring containing at least three, and at most seven, ring carbon atoms. Examples of cycloalkyl and cycloalkenyl as used herein include, but are not limited to, cyclopropyl, cyclobutyl, cyclopentyl, cyclopentenyl, cyclohexyl, cyclohexenyl, cycloheptyl and cycloheptenyl. The cycloalkyl and cycloalkenyl groups are optionally substituted as described hereinabove for alkyl and alkenyl groups.

Aryl groups referred to herein (individually or as part of another group) include single and fused rings suitably containing from 4 to 7, preferably 5 or 6, ring atoms in each ring, which rings may each be unsubstituted or substituted by, for example, up to three substituents. A fused ring system may include aliphatic rings and need include only one aromatic ring. Representative aryl groups include phenyl and naphthyl such as 1-naphthyl or 2-naphthyl.

Suitably any aryl group, including phenyl and naphthyl, may be optionally substituted by up to five, preferably up to three substituents. Suitable substituents include halogen, $(C_{1-6})$alkyl, aryl, aryl$(C_{1-6})$alkyl, $(C_{1-6})$alkoxy, $(C_{1-6})$alkoxy $(C_{1-6})$alkyl, halo$(C_{1-6})$alkyl, aryl$(C_{1-6})$alkoxy, hydroxy, nitro, cyano, azido, amino, mono- and di-N—$(C_{1-6})$alkylamino, acylamino, arylcarbonylamino, acyloxy, carboxy, carboxy salts, carboxy esters, carbamoyl, mono- and di-N—$(C_{1-6})$alkylcarbamoyl, $(C_{1-6})$alkoxycarbonyl, aryloxycarbonyl, ureido, guanidino, sulphonylamino, aminosulphonyl, $(C_{1-6})$alkylthio, $(C_{1-6})$alkylsulphinyl, $(C_{1-6})$alkylsulphonyl, heterocyclyl and heterocyclyl$(C_{1-6})$alkyl. In addition, two adjacent ring carbon atoms may be linked by a $(C_{3-5})$alkylene chain, to form a carbocyclic ring.

Heterocyclyl and heterocyclic groups referred to herein (individually or as part of another group) include, unless otherwise defined, aromatic and non-aromatic, single and fused, rings suitably containing up to four heteroatoms in each ring, each of which is selected from oxygen, nitrogen and sulphur, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring. Examples of aromatic heterocyclyl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. Examples of fused aromatic heterocyclyl rings include, but are not limited to, indolyl, isoindolyl, azaindolyl, benzoxazolyl, benzimidazolyl, benzothiazolyl, benzofuranyl, benzothiophenyl, quinolyl, isoquinolyl, quinazolinyl, cinnolinyl and phthalazinyl, in particular benzofuranyl. Examples of non-aromatic heterocyclyl groups include, but are not limited to, aziridinyl, pyrrolinyl, pyrrolidinyl, imidazolinyl, imidazolidinyl, pyrazolinyl, pyrazolidinyl, piperidyl, piperazinyl, morpholino, tetrahydropyranyl, tetrahydrofuranyl and thiomorpholino.

Preferably substituents for a heterocyclyl group are selected from halogen, $(C_{1-6})$alkyl, aryl$(C_{1-6})$alkyl, $(C_{1-6})$alkoxy, $(C_{1-6})$alkoxy$(C_{1-6})$alkyl, halo$(C_{1-6})$alkyl, hydroxy, amino, mono- and di-N—$(C_{1-6})$alkyl-amino, acylamino, carboxy, carboxy salts, carboxy esters, carbamoyl, mono- and di-N—$(C_{1-6})$alkylcarbonyl, aryloxycarbonyl, $(C_{1-6})$alkoxycarbonyl$(C_{1-6})$alkyl, aryl, oxy groups, ureido, guanidino, sulphonylamino, aminosulphonyl, $(C_{1-6})$alkylthio, $(C_{1-6})$alkylsulphinyl, $(C_{1-6})$alkylsulphonyl, heterocyclyl and heterocyclyl$(C_{1-6})$alkyl.

Acyl groups referred to herein (individually or as part of another group) include $(C_{1-6})$alkylcarbonyl. The acyl groups are optionally substituted by from one to three halogen atoms.

Halogen or halo groups referred to herein (individually or as part of another group) include fluorine, chlorine, bromine and iodine.

Depending on the position of attachment of substituents, two or more diastereoisomers may be possible. In that situation the present invention includes the individual diastereoisomers and mixtures thereof.

The 2-hydroxy compounds of formula (IA) may be of the (2S) configuration or the (2R) configuration, or be provided as mixtures thereof. The (2S) configuration is preferred.

Phase transfer catalysis systems are well known in the art, see for instance "Phase Transfer Catalysis", editor C M Starks, ACS Symposium Series 326, American Chemical Society, 1987. Preferably, the phase transfer catalysis system according to the process of the present invention comprises a solution of a compound of formula (IIA) or (IIB) and a phase transfer catalyst in an organic solvent such as dichloromethane, tert-butylmethyl ether, MIBK (4-methyl-2-pentanone) or toluene, an acidic aqueous solution of a thiol compound of formula (III) or an aqueous solution of an acid addition salt of a thiol compound of formula (III), and an aqueous solution of an inorganic base such as sodium hydroxide. Generally, in the process according to the present invention, the solution of the compound of formula (IIA) or (IIB) and the phase transfer catalyst in an organic solvent, and the acidic aqueous solution of the thiol compound of formula (III) or the aqueous solution of an acid addition salt of a thiol compound of formula (III), are mixed and the aqueous solution of the inorganic base is then added to adjust the pH. The phase transfer catalyst may be, for example, a quaternary ammonium salt.

Quaternary ammonium salts suitable for use in the process according to the present invention include tetra-$C_{(1-6)}$alkyl ammonium salts such as a tetra-methyl ammonium, methyltri-ethyl ammonium, methyltri-butyl ammonium or tetra-butyl ammonium halide or hydrogensulfate, for example tetra-butyl ammonium chloride or hydrogensulfate, in particular tetra-butyl ammonium hydrogensulfate. Preferably, the phase transfer catalyst is used in the range 0.5 to 15 mol %, more preferably 1 to 10 mol %, most preferably 3 to 6 mol %.

The acidic aqueous solution of a thiol compound of formula (III) generally has a pH of from 0.5 to 3, preferably from 0.5 to 1.5, more preferably about 1. The solution may be acidified by addition of a suitable inorganic acid such as hydrochloric acid.

The aqueous solution of an acid addition salt of a thiol compound of formula (III) is preferably an aqueous solution of the hydrochloride salt.

The solution of an inorganic base, for example an aqueous solution of sodium hydroxide, is added to adjust the pH of the reaction mixture so that the reaction mixture is alkaline. The pH of the reaction mixture is preferably adjusted to a pH of 12 to 14, preferably 12.5 to 13.5, more preferably about 13. During the course of the reaction it may be necessary to monitor the pH and add further portions of the solution of the inorganic base in order to maintain the pH at the desired level.

The phase transfer catalysis process is generally carried out at a temperature of up to 40° C. In one embodiment, the process is carried out at a temperature of from 15 to 30° C. In another embodiment, the process is carried out at a temperature in the range 0 to 25° C., for example 10 to 25° C.

Those skilled in the art will appreciate that in the process according to the present invention it may be necessary and/or desirable to protect one or more sensitive groups in the molecule to prevent undesirable side reactions. Suitable protecting groups for use according to the present invention are well known to those skilled in the art and which may be removed under conventional conditions without disrupting the remainder of the molecule. A comprehensive discussion of the ways in which groups may be protected and methods for cleaving the resulting protected derivatives is given in for example "Protective Groups in Organic Chemistry" by T. W. Greene (Wiley-Interscience, New York, 2nd edition, 1991) or "Protecting Groups" by P. J. Kocienski (Georg Thieme Verlag 1994). Particularly suitable hydroxy protecting groups include triorganosilyl groups (e.g. trialkylsilyl such as trimethylsilyl or tert-butyldimethylsilyl), organocarbonyl and organooxycarbonyl groups such as acetyl, allyloxycarbonyl, 4-methoxybenzyloxycarbonyl and 4-nitrobenzyloxycarbonyl, and alkyl ethers such as tetrahydropyranyl or tert-butyl. Particularly suitable carboxy protecting groups include alkyl and aryl groups, for instance methyl, ethyl and phenyl. Particularly suitable amino protecting groups include acyl type protecting groups (e.g. formyl, trifluoroacetyl or acetyl), aromatic urethane type protecting groups (e.g. benzyloxycarbonyl (Cbz) and substituted Cbz such as 4-methoxybenzyloxycarbonyl or 4-nitrobenzyloxycarbonyl), aliphatic urethane protecting groups (e.g. 9-fluorenylmethoxycarbonyl (Fmoc), alkoxycarbonyl such as t-butyloxycarbonyl (Boc) or isopropyloxycarbonyl, and cyclohexyloxycarbonyl) and alkyl type protecting groups (e.g. benzyl, trityl and chlorotrityl).

In the compound of formula (IIA) or (IIB), representative values of Y when a hydroxy protecting group include acyl, so that for example —OY may be trifluoroacetyloxy or dichloroacetyloxy. When the intended $R^3$ is also hydroxyl, then it may be useful to have $R^{3A}$ as acyloxy, for example acetyl or dichloroacetyl. When however the process is used to prepare the preferred compound, mutilin 14-(exo-8-methyl-8-azabicyclo[3.2.1]oct-3-ylsulfanyl)-acetate, Y is preferably hydrogen.

$R^{1A}$ is typically the $R^1$ group vinyl. This group may be converted to the alternative $R^1$ ethyl group by hydrogenating the vinyl group to form an ethyl group, for example by hydrogenation over a palladium catalyst (e.g. 10% palladium-on-carbon) in a solvent such as ethyl acetate, ethanol, dioxane, or tetrahydrofuran.

$R^{3A}$ is typically hydrogen or protected hydroxyl, such as acyloxy. After the coupling reaction, acyl protecting groups may be removed to give the hydroxyl groups by hydrolysis, for example using sodium hydroxide in methanol.

It may also be necessary to protect substituent groups in the compound of formula (III) prior to reaction with the compound (IIA) or (IIB), for example protecting nitrogen atoms with alkoxycarbonyl, for example t-butoxycarbonyl.

In another embodiment of the present invention the above process may be carried out by reacting a compound of formula (IIC):

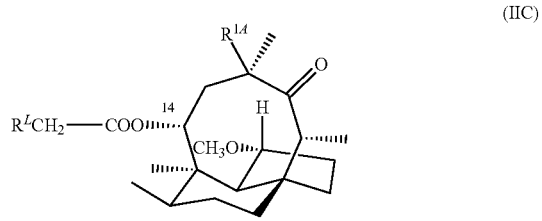

(IIC)

in which:
$R^{1A}$ and $R^L$ are as defined for formulae (IIA) and (IIB); with a compound of formula (III) as hereinbefore defined in which $R^{2A}$ is $R^2$ as defined for formulae (IA) and (IB), in a phase transfer catalysis system as hereinbefore defined, and then treating the product with an acid;
and thereafter, where required or desired,
converting an $R^{1A}$ group to an $R^1$, and/or
converting one $R^1$ group to another $R^1$ group.

The acid treatment referred to above converts the epimutilin configuration of formula (IIC) to the usual mutilin nucleus of formula (IIA). Typically this conversion is carried out by treatment with concentrated HCl or Lukas reagent (concentrated HCl saturated with $ZnCl_2$) in dioxane.

As in formulae (IIA) and (IIB), $R^{1A}$ is typically the $R^1$ group vinyl, and this may be converted to the alternative $R^1$ group by hydrogenating the vinyl group to form an ethyl group.

It will be appreciated that it may be necessary to convert an $R^{1A}$, $R^{2A}$ or $R^{3A}$ group to an $R^1$, $R^2$ or $R^3$ group. The groups may be converted using standard functional group transformations.

It will also be appreciated that it may be necessary to interconvert one $R^1$, $R^2$ or $R^3$ group to another $R^1$, $R^2$ or $R^3$ group. This typically arises when one compound of formula (IA/B) is used as the immediate precursor of another compound of formula (IA/B) or when it is easier to introduce a more complex or reactive substituent at the end of a synthetic sequence. A substituent group in $R^2$ can be converted into another substituent group using one of the general methods for functional group transformation described in the literature (e.g. a carboxylic ester can be hydrolysed to a carboxylic acid with base; an acid can be converted into an amide; a tert-butoxycarbonylamino group can be converted into an amine by treatment with trifluoroacetic acid; an amino group can be alkylated or acylated), provided that the method chosen is compatible with other functional groups in the molecule (e.g. the ketone at C-3 in the pleuromutilin nucleus).

Functional group transformations are well known in the art and are described in, for instance, *Comprehensive Organic Functional Group Transformations*, eds. A. R. Katritzky, O.

Meth-Cohn, and C. W. Rees (Elsevier Science Ltd., Oxford, 1995), *Comprehensive Organic Chemistry*, eds. D. Barton and W. D. Ollis (Pergamon Press, Oxford, 1979), and *Comprehensive Organic Transformations*, R. C. Larock (VCH Publishers Inc., New York, 1989).

Preferably, the process according to the present invention is used to prepare a compound of formula (IA), in particular mutilin 14-(exo-8-methyl-8-azabicyclo[3.2.1]oct-3-ylsulfanyl)-acetate.

The preparation of compounds of formulae (IIA), (IIB) and (IIC) is described in WO99/21855. In a preferred embodiment of the present invention, a compound of formula (IIA) wherein $R^L$ is $CH_3SO_2O$ is prepared by reacting pleuromutilin with methane sulphonyl chloride.

Thiol compounds of formula (III) may be readily prepared from the corresponding compounds of formula (IV):

$$R^{2A}-(CH_2)_m-X \qquad (IV)$$

in which:
$R^{2A}$ is $R^2$ as defined for formulae (IA) and (IB) or a group convertible to $R^2$;
m is as defined for formulae (IA) and (IB); and
X is a functional group which can be converted to thiol, either directly or indirectly; using conventional functional group interconversion processes for converting X to a thiol group.

Examples of suitable X groups include hydroxy, xanthate, thioacetate and leaving groups such as mesylate.

Preferably, the thiol compound of formula (III) is prepared in a novel process from the corresponding xanthate compound.

Thus in another embodiment the present invention provides a process for preparing a compound of formula (III) as hereinbefore defined which process comprises hydrolysis of a compound of formula (IV) in which X is —$SCSOC_{(1-6)}$alkyl.

Preferably, the hydrolysis is carried out using a solution of an inorganic base such as sodium or potassium hydroxide in a solvent such as ethanol, ethanol/toluene or ethanol/MIBK.

Preferably, the xanthate group X is —$SCSOC_{(1-4)}$alkyl, in particular —$SCSOCH_2CH_3$.

Alternatively, the thiol compound of formula (III) may be prepared from the corresponding thioacetate ester by hydrolysis with an alkali metal alkoxide in an alcohol solvent, for instance potassium t-butoxide or sodium methoxide in ethanol.

Preferably, the thiol compound of formula (III) is not isolated but is used in the next step as the crude reaction product. If necessary, the thiol compound may be prepared in a more purified form, by isolation as an acid addition salt, for instance the hydrochloride salt. The thiol compound may also be isolated as the sodium salt.

In another embodiment the present invention provides a process for the preparation of a compound of formula (IA) or (IB) as hereinbefore defined which process comprises, as an early step, the preparation of a thiol compound of formula (III) from a compound of formula (IV) in which X is a xanthate group, as hereinbefore defined. The resultant thiol may be then reacted with a compound of formula (IIA/B/C) in a phase transfer catalysis process, as hereinbefore defined, or reacted with a compound of formula (IIA/B/C) in the presence of an inorganic base, such as sodium methoxide, sodium ethoxide, sodium hydride, sodium hexamethyldi-silazide or lithium hexamethyldi-silazide, in a solvent such as 2-propanol, ethanol, methanol, N,N-dimethylformamide or tetrahydrofuran, as described in WO99/21855.

In another embodiment the present invention provides an acid addition salt of a compound of formula (III). Preferably, the acid addition salt is the hydrochloride salt.

In another embodiment the present invention provides the sodium salt of a compound of formula (III).

Xanthate compounds of formula (IV) in which X is —$SCSOC_{(1-6)}$alkyl may be readily prepared from the corresponding compound of formula (IV) in which X is a leaving group, for instance mesylate, by reaction with a xanthate salt such as sodium or potassium xanthate, in a solvent such toluene, MIBK, acetone, ethanol, THF, dioxane, DMSO, water or pyridine, in particular toluene. Preferably an excess of xanthate is used. In one embodiment, from 1.1 to 3 equivalents (by mole), for example from 1.1 to 2 equivalents such as about 1.2 equivalents of xanthate are used. In a further embodiment, from 1.3 to 3 equivalents, for example about 1.5 equivalents of xanthate are used. The reaction is typically carried out a temperature of from 25 to 50° C. In one embodiment, a temperature of from 25 to 35° C., for example about 30° C. is used. In a further embodiment, a temperature of from 35 to 40° C. is used. The mesylate compound of formula (IV) in turn may be prepared by reaction of the corresponding alcohol with methanesulfonyl chloride in dichloromethane, in the presence of a base such as triethylamine or Hunig's base (diisopropylethylamine).

Preferably, the mesylate compound of formula (IV) is carried through to the pleuromutilin compound of formula (IA) or (IB) via the xanthate intermediate in a "one-pot" synthesis.

In another embodiment the present invention provides a process for the preparation of a compound of formula (IA) or (IB) as hereinbefore defined which process comprises, as an early step, the preparation of a compound of formula (IV) in which X is a xanthate group from a compound of formula (IV) wherein X is a mesylate group, as hereinbefore defined.

In another embodiment the present invention provides a process for the preparation of a compound of formula (IA) or (IB) as hereinbefore defined which process comprises, as an early step, the preparation of a compound of formula (IV) in which X is a mesylate group from a compound of formula (IV) wherein X is a hydroxy group, as hereinbefore defined.

In another embodiment the present invention provides a compound of formula (IV) in which X is —$SCSOC_{(1-6)}$alkyl, or an acid addition salt thereof, for example an acid addition salt of tropine ethylxanthate, in particular the maleate salt.

Thioacetate compounds of formula (IV) may be readily prepared from the corresponding mesylate in a novel process. Accordingly, in another embodiment the present invention provides a process for preparing a compound of formula (IV) in which X is —$SCOC_{(1-6)}$alkyl which process comprises reacting a compound of formula (IV) in which X is a leaving group, for example mesylate, with a thioacetate salt such as potassium thioacetate, in a solvent, for instance acetone or, more preferably, acetonitrile/water or pyridine/water, at a temperature of from 30 to 60° C., preferably from 35 to 50° C.

Alternatively, a thioacetate compound of formula (IV) may be prepared directly from the corresponding compound of formula (IV) in which X is hydroxy by treatment with thiolacetic acid in the presence of an activating system, for instance triphenylphosphine/di-iso-propyl azodicarboxylate, as described in WO99/21855.

In a preferred embodiment the process according to the present invention is used to prepare mutilin 14-(exo-8-methyl-8-azabicyclo[3.2.1]oct-3-ylsulfanyl)-acetate (compound of formula (C)). In order to provide the required exo stereochemistry in the final product, tropine-3-thiol is typically used as the compound of formula (III). We have found that, on a development scale, the preferred route via the xanthate intermediate gives a yield of final compound of about 70% (from pleuromutilin) and 35% (from tropine), compared to about 25% (from pleuromutilin) and 9% (from tropine) using the alternative route via a thioacetate intermediate.

Impure compound of formula (IA) or (IB), in particular mutilin 14-(exo-8-methyl-8-azabicyclo[3.2.1]oct-3-ylsulfanyl)-acetate, may be purified by a process which comprises partitioning between an organic solvent such as ethyl acetate and an acidic aqueous phase, retaining the acidic aqueous phase, mixing with an organic solvent such as dichloromethane, and then making the aqueous phase basic with an inorganic base such as sodium carbonate and finally back extracting into the organic solvent. This organic solution may then be concentrated under reduced pressure, to give residue which can then be crystallised to provide pure crystalline product. For mutilin 14-(exo-8-methyl-8-azabicyclo[3.2.1]oct-3-ylsulfanyl)-acetate, the preferred solvent system is isopropanol/water.

Alternatively, impure compound of formula (IA) or (IB) may be purified by recrystallisation from a suitable solvent, for example ethanol/water, an alcohol such as isopropanol or an ester such as isopropyl acetate.

WO99/21855 describes the preparation of mutilin 14-(exo-8-methyl-8-azabicyclo[3.2.1]oct-3-ylsulfanyl)-acetate in small scale reactions in which the product is isolated by chromatography without further purification. The compounds prepared according to the process of the present invention may however be in crystalline form and may optionally be hydrated or solvated. Furthermore, some of the crystalline forms of the compounds of formula (IA) and (IB) prepared according to the process of the present invention may exist as polymorphs, which are included in the present invention.

Thus in another embodiment the present invention provides crystalline mutilin 14-(exo-8-methyl-8-azabicyclo[3.2.1]oct-3-ylsulfanyl)-acetate.

In a further embodiment the present invention provides crystalline mutilin 14-(exo-8-methyl-8-azabicyclo[3.2.1]oct-3-ylsulfanyl)-acetate characterised in that it provides:
(i) an infra-red spectrum measured by ATR (attenuated total reflectance) containing peaks at 3234, 1735 and 1725 cm$^{-1}$, and/or
(ii) a DSC (differential scanning calorimetry) profile having an endotherm with an onset temperature of 125-127° C., and/or
(iii) an XRPD (X-ray powder diffraction) pattern having peaks at about 9.6, about 12.8, about 13.9 and about 19.6.

In one preferred embodiment the present invention provides crystalline mutilin 14-(exo-8-methyl-8-azabicyclo[3.2.1]oct-3-ylsulfanyl)-acetate characterised in that it provides an infra-red spectrum substantially in accordance with FIG. 1.

Figure 2:
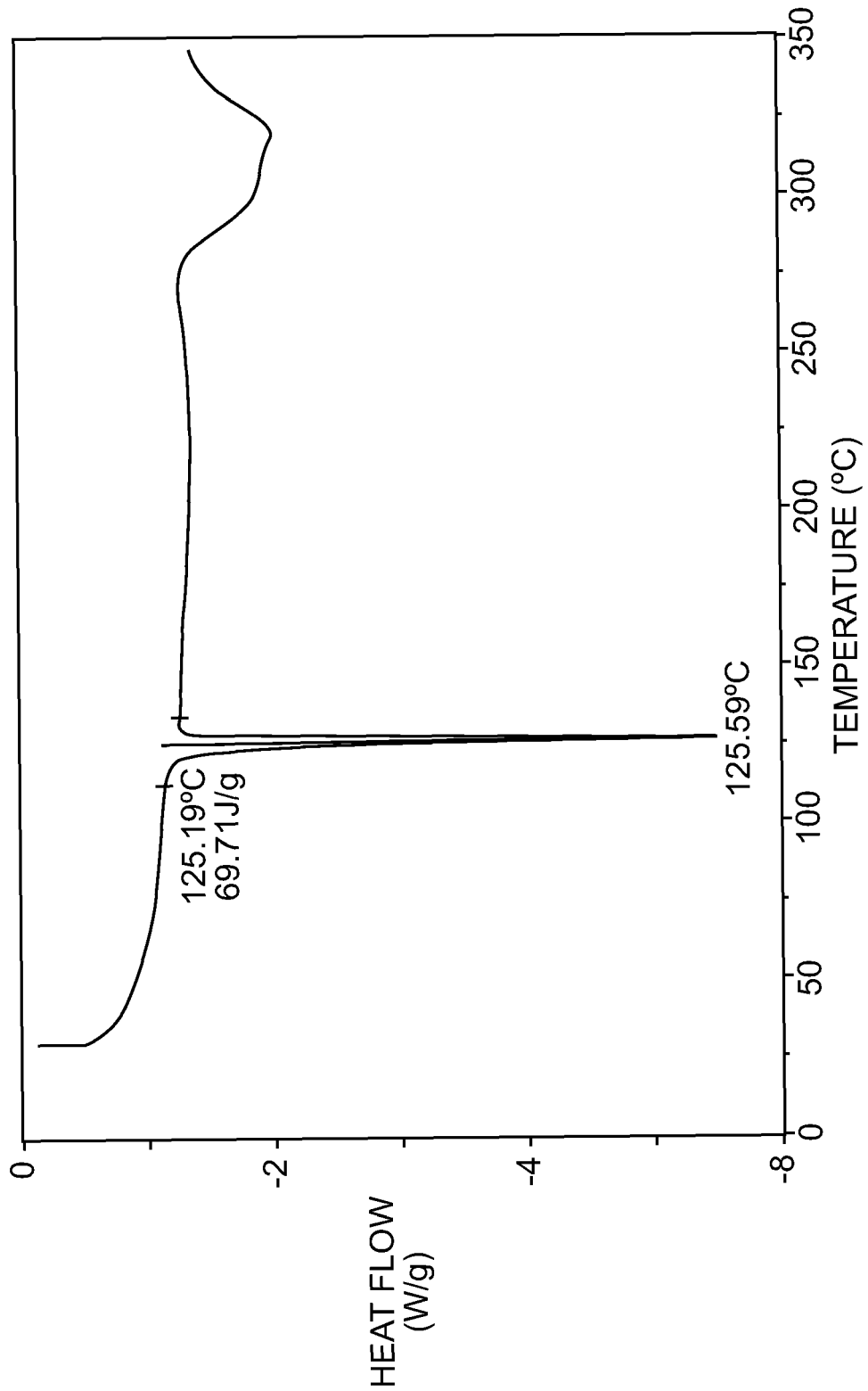
FIG. 2 is a DSC thermogram of crystalline mutilin 14-(exo-8-methyl-8-azabicyclo[3.2.1]oct-3-ylsulfanyl)-acetate.

In another preferred embodiment the present invention provides crystalline mutilin 14-(exo-8-methyl-8-azabicyclo[3.2.1]oct-3-ylsulfanyl)-acetate characterised in that it provides a DSC profile substantially in accordance with FIG. 2.

Figure 3:
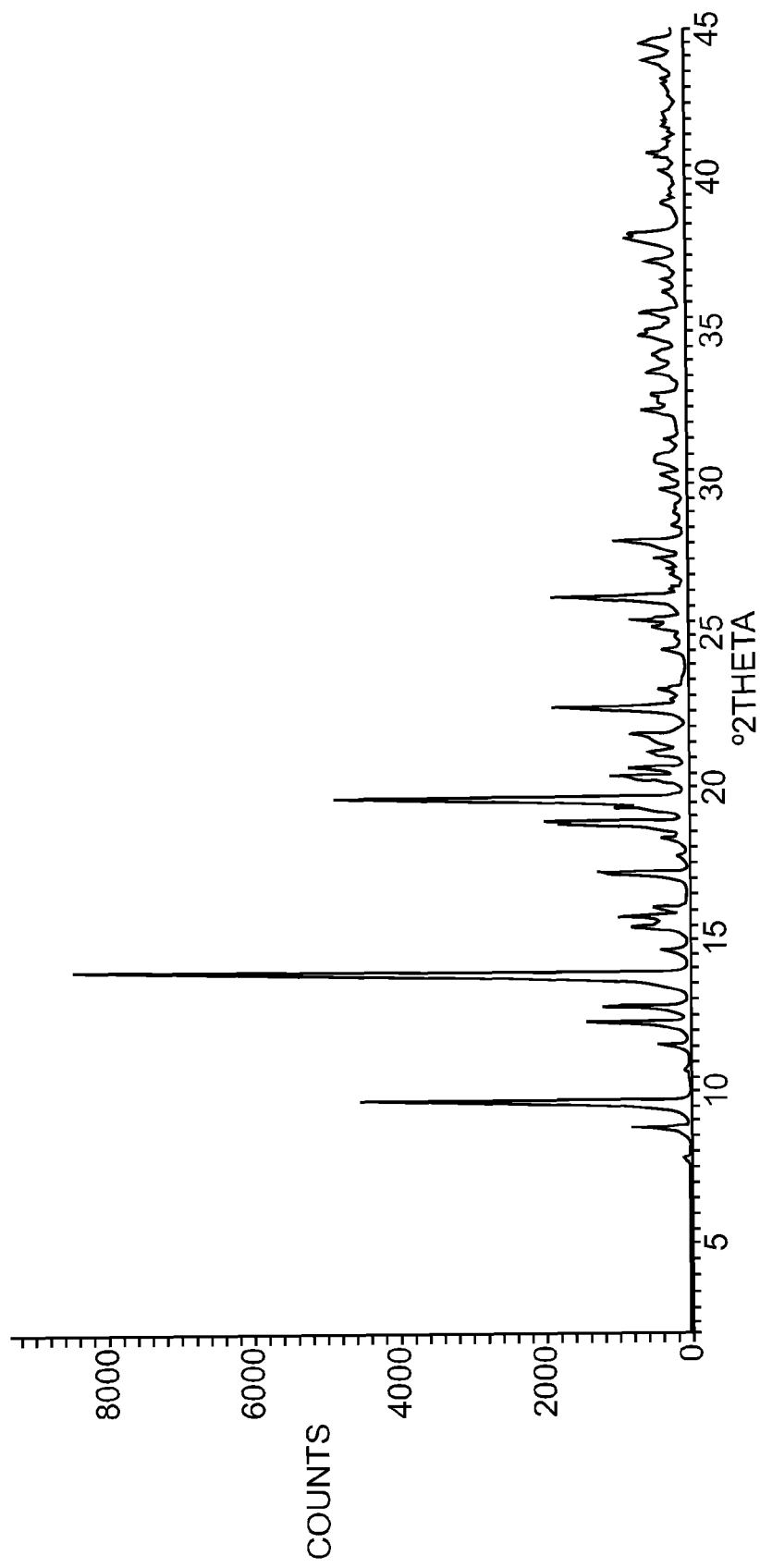
FIG. 3 is an XRPD pattern of crystalline mutilin 14-(exo-8-methyl-8-azabicyclo[3.2.1]oct-3-ylsulfanyl)-acetate.

In a further preferred embodiment the present invention provides crystalline mutilin 14-(exo-8-methyl-8-azabicyclo[3.2.1]oct-3-ylsulfanyl)-acetate characterised in that it provides an XRPD pattern substantially in accordance with FIG. 3.

According to a second aspect of the present invention we have found that certain salts of mutilin 14-(exo-8-methyl-8-azabicyclo[3.2.1]oct-3-ylsulfanyl)-acetate have advantages which render them especially suitable for use in medical therapy, in particular antibacterial therapy, and in the preparation of pharmaceutical compositions. In particular, the hydrosuccinate salt of mutilin 14-(exo-8-methyl-8-azabicyclo[3.2.1]oct-3-ylsulfanyl)-acetate is readily prepared in a stable, non-hygroscopic crystalline form, has a high solubility in water and does not cause significant irritation when applied as a suitable topical formulation.

Thus in one embodiment of the present invention there is provided a pharmaceutically acceptable salt of mutilin 14-(exo-8-methyl-8-azabicyclo[3.2.1]oct-3-ylsulfanyl)-acetate selected from the acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, dihydrochloride, edetate, edisylate, estolate, esylate, ethanedisulfonate, ethanesulfonate, formate, fumarate, gluceptate, gluconate, glutamate, glycollate, glycollylarsanilate, hexylresorcinate, hydrabamine, hydrobromide, hydrochloride, hydrofumarate, hydrogen phosphate, hydroiodide, hydromaleate, hydrosuccinate, hydroxynaphthoate, isethionate, itaconate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, oxaloacetate, pamoate (embonate), palmate, palmitate, pantothenate, phosphate/diphosphate, piruvate, polygalacturonate, propionate, saccharate, salicylate, stearate, subacetate, succinate, sulfate, tannate, tartrate, teoclate, tosylate, triethiodide, trifluoroacetate and valerate salts, or a solvate thereof.

In another embodiment of the present invention there is provided a pharmaceutically acceptable salt of mutilin 14-(exo-8-methyl-8-azabicyclo[3.2.1]oct-3-ylsulfanyl)-acetate selected from the acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, dihydrochloride, edetate, edisylate, estolate, esylate, ethanedisulfonate, ethanesulfonate, formate, fumarate, gluceptate, gluconate, glutamate, glycollate, glycollylarsanilate, hexylresorcinate, hydrabamine, hydrobromide, hydrofumarate, hydrogen phosphate, hydroiodide, hydromaleate, hydrosuccinate, hydroxynaphthoate, isethionate, itaconate, lactate, lactobionate, laurate, malate, mandelate, methylbromide, methylnitrate, methylsulfate, monopotassium maleate, mucate, napsylate, nitrate, N-methylglucamine, oxalate, oxaloacetate, pamoate (embonate), palmate, palmitate, pantothenate, phosphate/diphosphate, piruvate, polygalacturonate, propionate, saccharate, salicylate, stearate, subacetate, succinate, sulfate, tannate, tartrate, teoclate, tosylate, triethiodide, trifluoroacetate and valerate salts, or a solvate thereof.

Preferred salts according to the present invention include the hydrosuccinate, hydrofumarate, hydromaleate and tosylate salts, especially the hydrosuccinate, hydrofumarate and tosylate salts.

A particularly preferred salt according to the present invention is the hydrosuccinate salt.

For the avoidance of doubt, as used herein, the hydrosuccinate salt of mutilin 14-(exo-8-methyl-8-azabicyclo[3.2.1]oct-3-ylsulfanyl)-acetate is the salt formed between mutilin 14-(exo-8-methyl-8-azabicyclo[3.2.1]oct-3-ylsulfanyl)-acetate and succinic acid in a stoichiometric ratio of 1:1. Similarly, the hydrofumarate and hydromaleate salts of mutilin 14-(exo-8-methyl-8-azabicyclo[3.2.1]oct-3-ylsulfanyl)-acetate are the salts formed between mutilin 14-(exo-8-methyl-8-azabicyclo[3.2.1]oct-3-ylsulfanyl)-acetate and fumaric or maleic acids respectively in a stoichiometric ratio of 1:1

The salts of the invention may be in crystalline or non-crystalline form and may optionally be solvated or hydrated. As discussed above, those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the salts of the invention are within the scope of the invention. This invention includes within its scope stoichiometric hydrates as well as salts containing variable amounts of water.

Furthermore, some of the crystalline forms of the salts may exist as polymorphs, which are included in the present invention.

Thus in another embodiment of the present invention there is provided a pharmaceutically acceptable salt of mutilin 14-(exo-8-methyl-8-azabicyclo[3.2.1]oct-3-ylsulfanyl)-acetate selected from the acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, dihydrochloride, edetate, edisylate, estolate, esylate, ethanedisulfonate, ethanesulfonate, formate, fumarate, gluceptate, gluconate, glutamate, glycollate, glycollylarsanilate, hexylresorcinate, hydrabamine, hydrobromide, hydrochloride, hydrofumarate, hydrogen phosphate, hydroiodide, hydromaleate, hydrosuccinate, hydroxynaphthoate, isethionate, itaconate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, oxaloacetate, pamoate (embonate), palmate, palmitate, pantothenate, phosphate/diphosphate, piruvate, polygalacturonate, propionate, saccharate, salicylate, stearate, subacetate, succinate, sulfate, tannate, tartrate, teoclate, tosylate, triethiodide, trifluoroacetate and valerate salts, or a solvate thereof, in crystalline form.

Preferred crystalline salts according to the present invention include the hydrosuccinate, hydrofumarate, hydromaleate and tosylate salts, especially the hydrosuccinate, hydrofumarate and tosylate salts.

A particularly preferred crystalline salt according to the present invention is the hydrosuccinate salt.

In another embodiment the present invention provides a crystalline hydrosuccinate salt of mutilin 14-(exo-8-methyl-8-azabicyclo[3.2.1]oct-3-ylsulfanyl)-acetate characterised in that it provides:
(i) an infra-red spectrum measured by ATR (attenuated total reflectance) containing peaks at 3470, 1731 and 1711 cm$^{-1}$, and/or
(ii) a DSC (differential scanning calorimetry) profile having an endotherm with an onset temperature of 168-170° C., and/or
(iii) an XRPD (X-ray powder diffraction) pattern having peaks at about 13.4, about 14.4 and about 20.7.

In another embodiment the present invention provides a crystalline hydrofumarate salt of mutilin 14-(exo-8-methyl-8-azabicyclo[3.2.1]oct-3-ylsulfanyl)-acetate characterised in that it provides:
(i) an infra-red spectrum measured by ATR (attenuated total reflectance) containing peaks at 3487, 1731 and 1710 cm$^{-1}$, and/or
(ii) a DSC (differential scanning calorimetry) profile having an endotherm with an onset temperature of 243-245° C., and/or
(iii) an XRPD (X-ray powder diffraction) pattern having peaks at about 13.5, about 14.4 and about 20.5.

In another embodiment the present invention provides a crystalline hydromaleate salt of mutilin 14-(exo-8-methyl-8-azabicyclo[3.2.1]oct-3-ylsulfanyl)-acetate characterised in that it provides:
(i) an infra-red spectrum measured by ATR (attenuated total reflectance) containing peaks at 3368, 1729 and 1709 cm$^{-1}$, and/or
(ii) a DSC (differential scanning calorimetry) profile having an endotherm with an onset temperature of 186-188° C., and/or
(iii) an XRPD (X-ray powder diffraction) pattern having peaks at about 13.5 and about 20.7.

In another embodiment the present invention provides a crystalline tosylate salt of mutilin 14-(exo-8-methyl-8-azabicyclo[3.2.1]oct-3-ylsulfanyl)-acetate characterised in that it provides:
(i) an infra-red spectrum measured by ATR (attenuated total reflectance) containing peaks at 3394, 1735 and 1715 cm$^{-1}$, and/or
(ii) a DSC (differential scanning calorimetry) profile having an endotherm with an onset temperature of 122-124° C., and/or
(iii) an XRPD (X-ray powder diffraction) pattern having peaks at about 14.0, about 16.2, about 18.5 and about 22.1.

Figure 4:
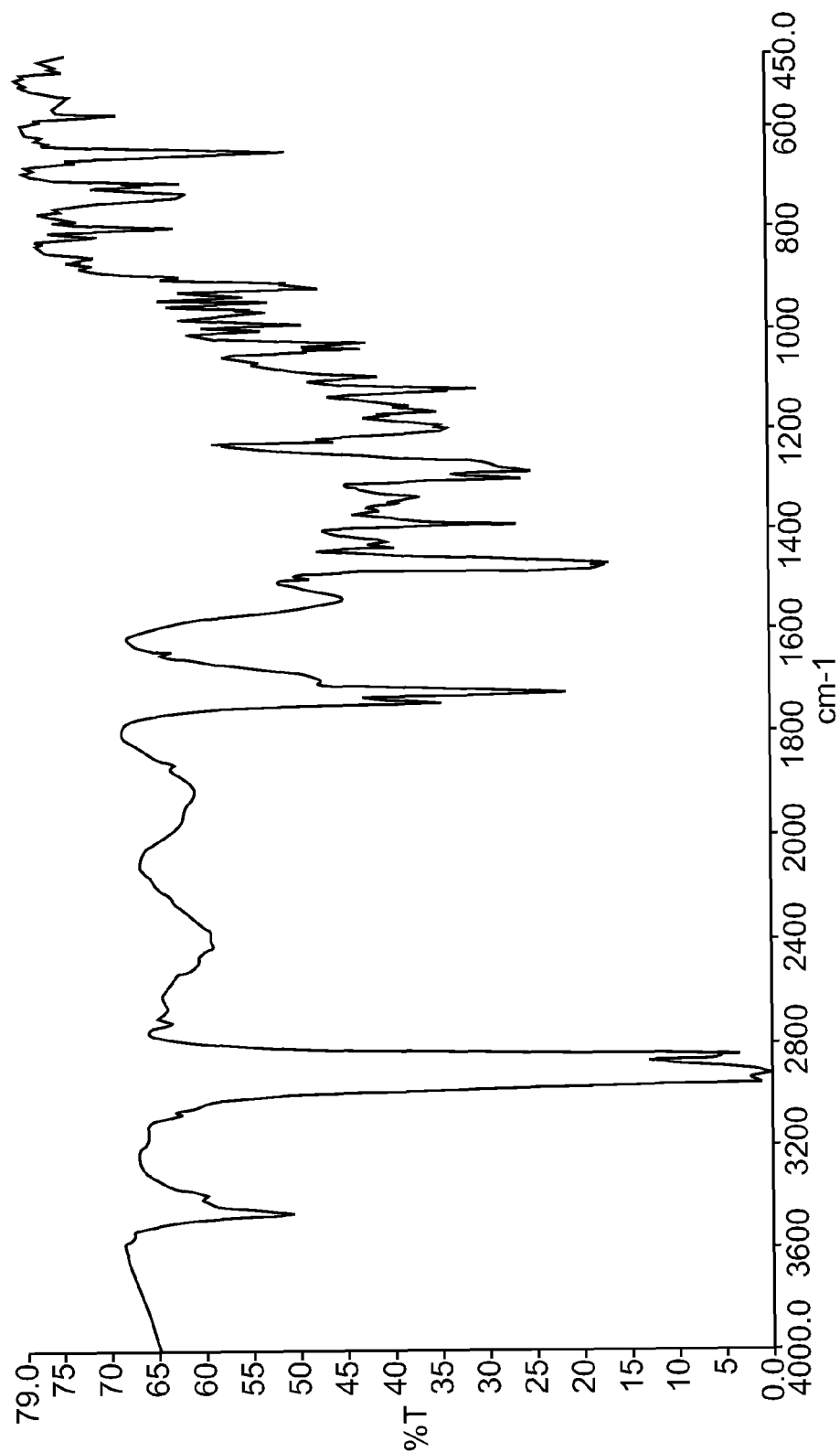
FIG. 4 is an infra-red spectrum of the crystalline hydrosuccinate salt of mutilin 14-(exo-8-methyl-8-azabicyclo[3.2.1] oct-3-ylsulfanyl)-acetate measured by ATR (attenuated total reflectance).

In one preferred embodiment the present invention provides a crystalline hydrosuccinate salt of mutilin 14-(exo-8-methyl-8-azabicyclo[3.2.1]oct-3-ylsulfanyl)-acetate characterised in that it provides an infra-red spectrum substantially in accordance with FIG. 4.

Figure 5:
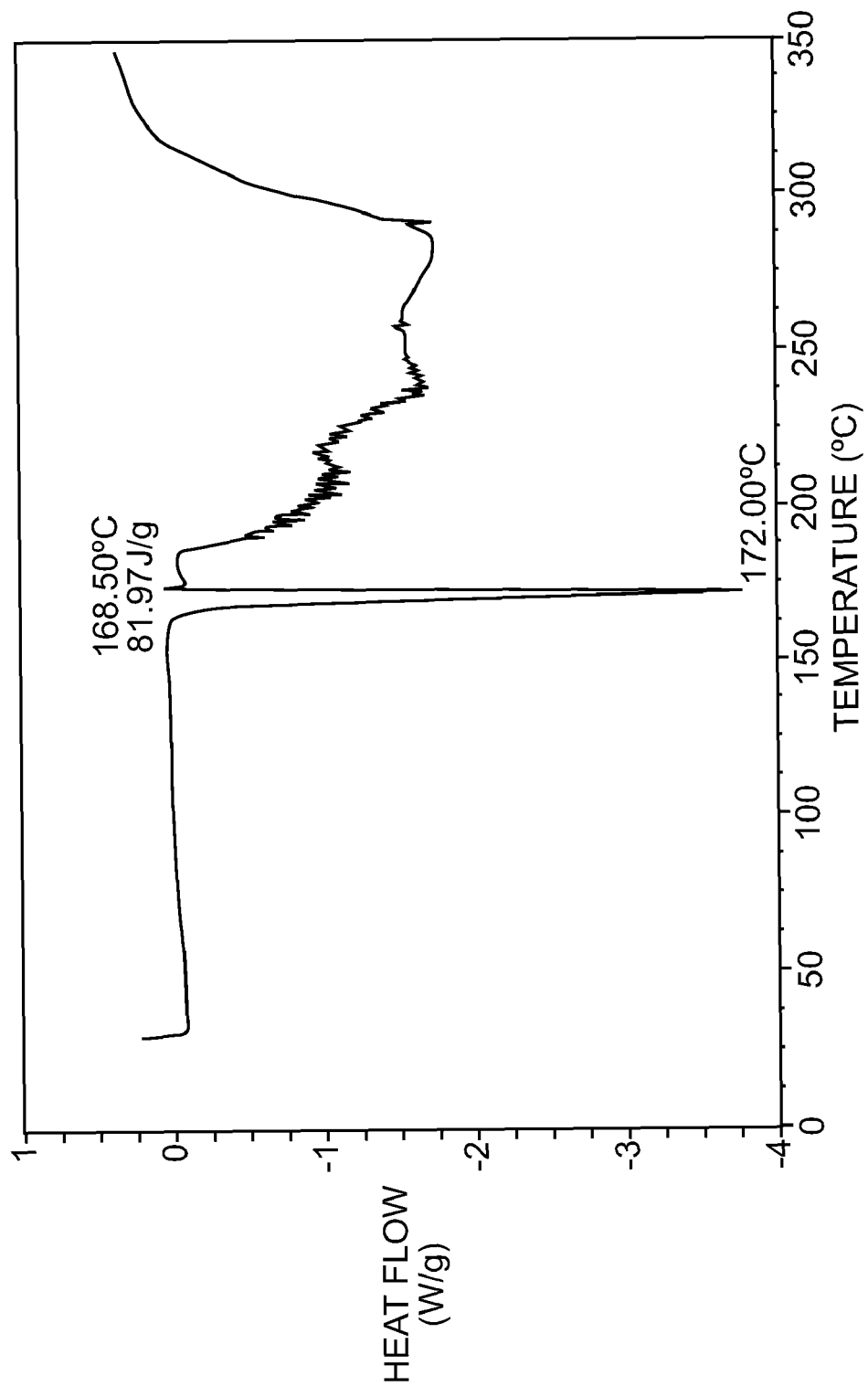
FIG. 5 is a DSC thermogram of the crystalline hydrosuccinate salt of mutilin 14-(exo-8-methyl-8-azabicyclo[3.2.1] oct-3-ylsulfanyl)-acetate.

In another preferred embodiment the present invention provides a crystalline hydrosuccinate salt of mutilin 14-(exo-8-methyl-8-azabicyclo[3.2.1]oct-3-ylsulfanyl)-acetate characterised in that it provides a DSC profile substantially in accordance with FIG. 5.

Figure 6:
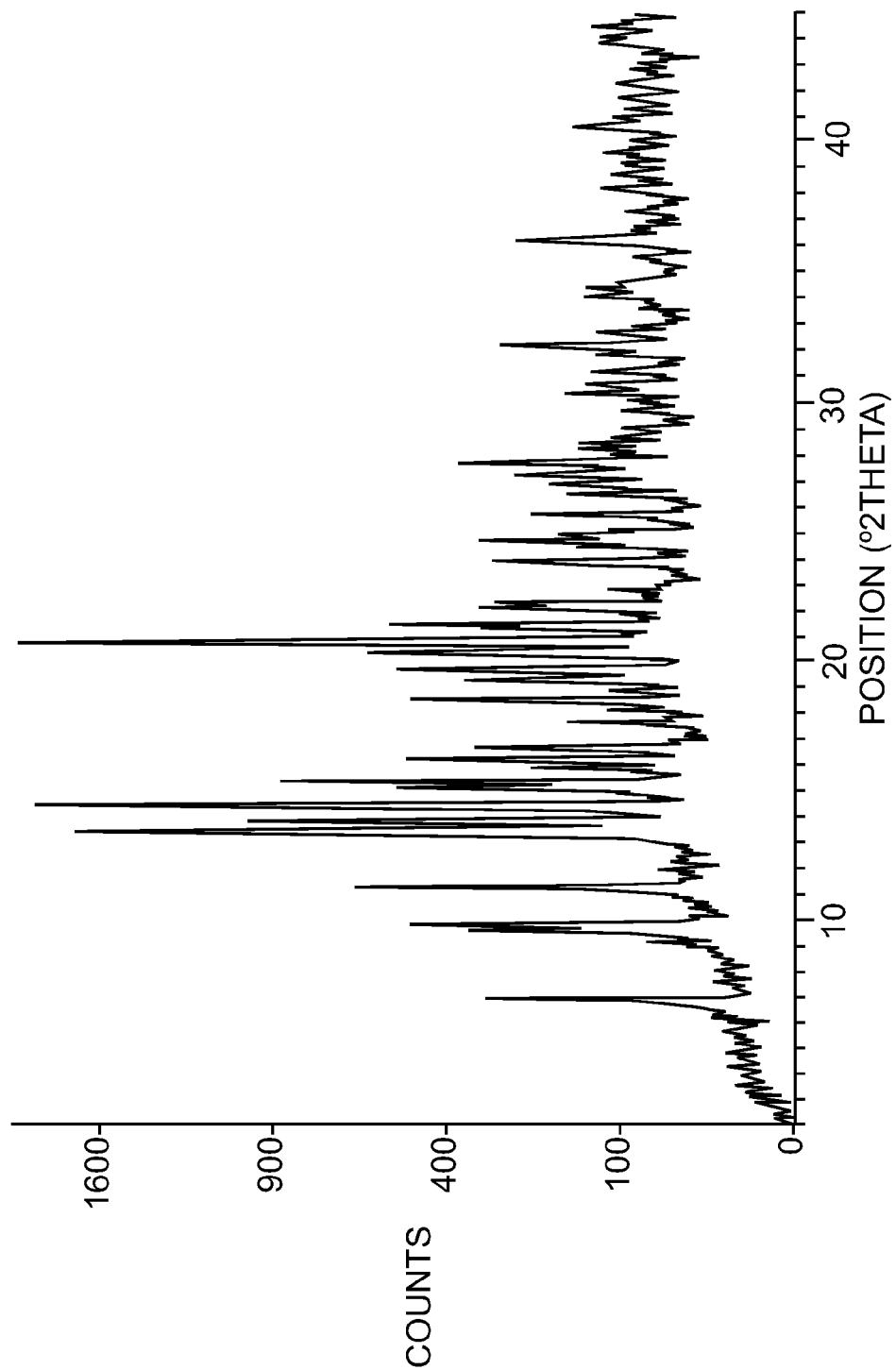
FIG. 6 is an XRPD pattern of the crystalline hydrosuccinate salt of mutilin 14-(exo-8-methyl-8-azabicyclo[3.2.1] oct-3-ylsulfanyl)-acetate.
Figure 7:
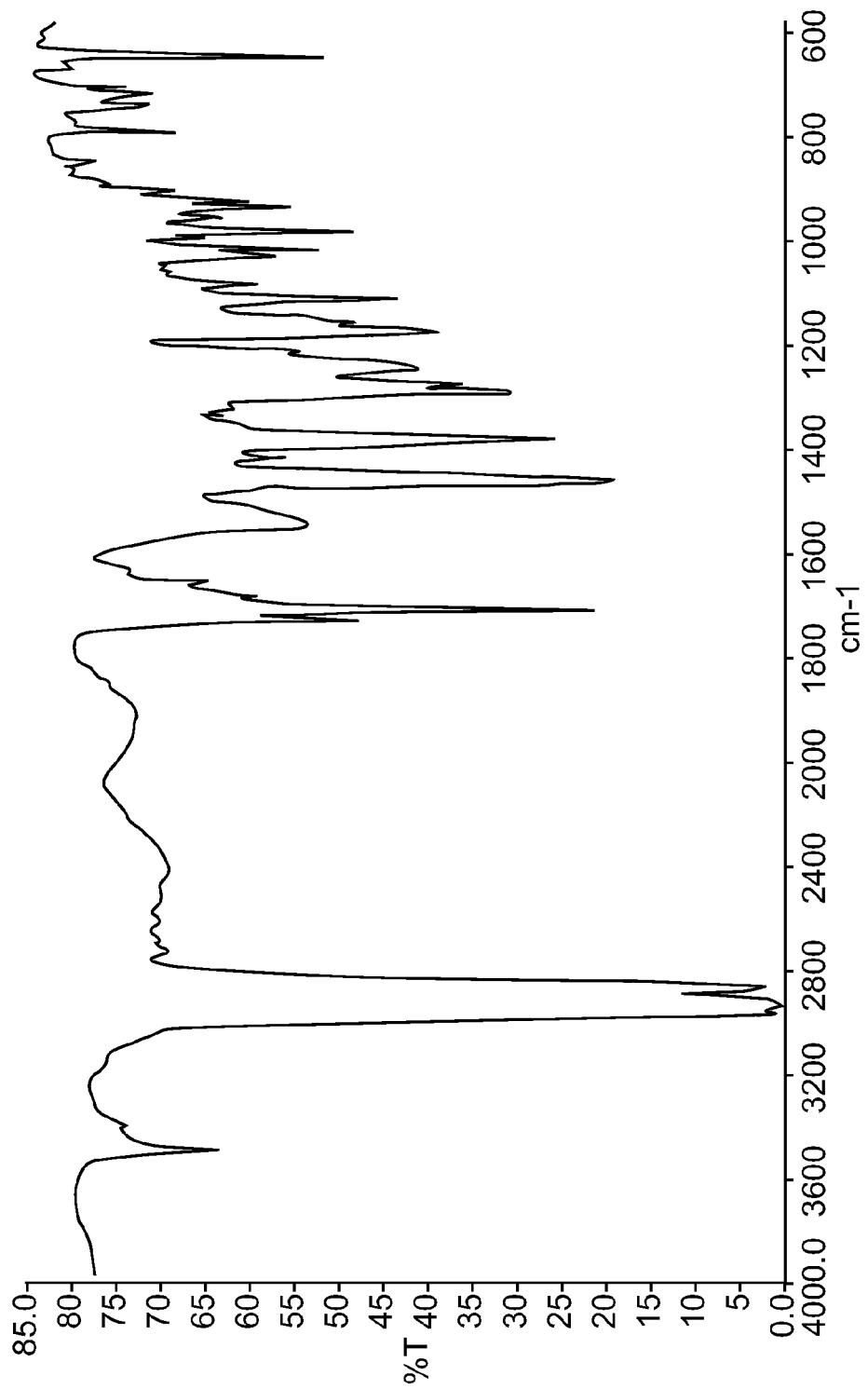
FIG. 7 is an infra-red spectrum of the crystalline hydrofumarate salt of mutilin 14-(exo-8-methyl-8-azabicyclo[3.2.1]oct-3-ylsulfanyl)-acetate measured by ATR (attenuated total reflectance).
Figure 8:
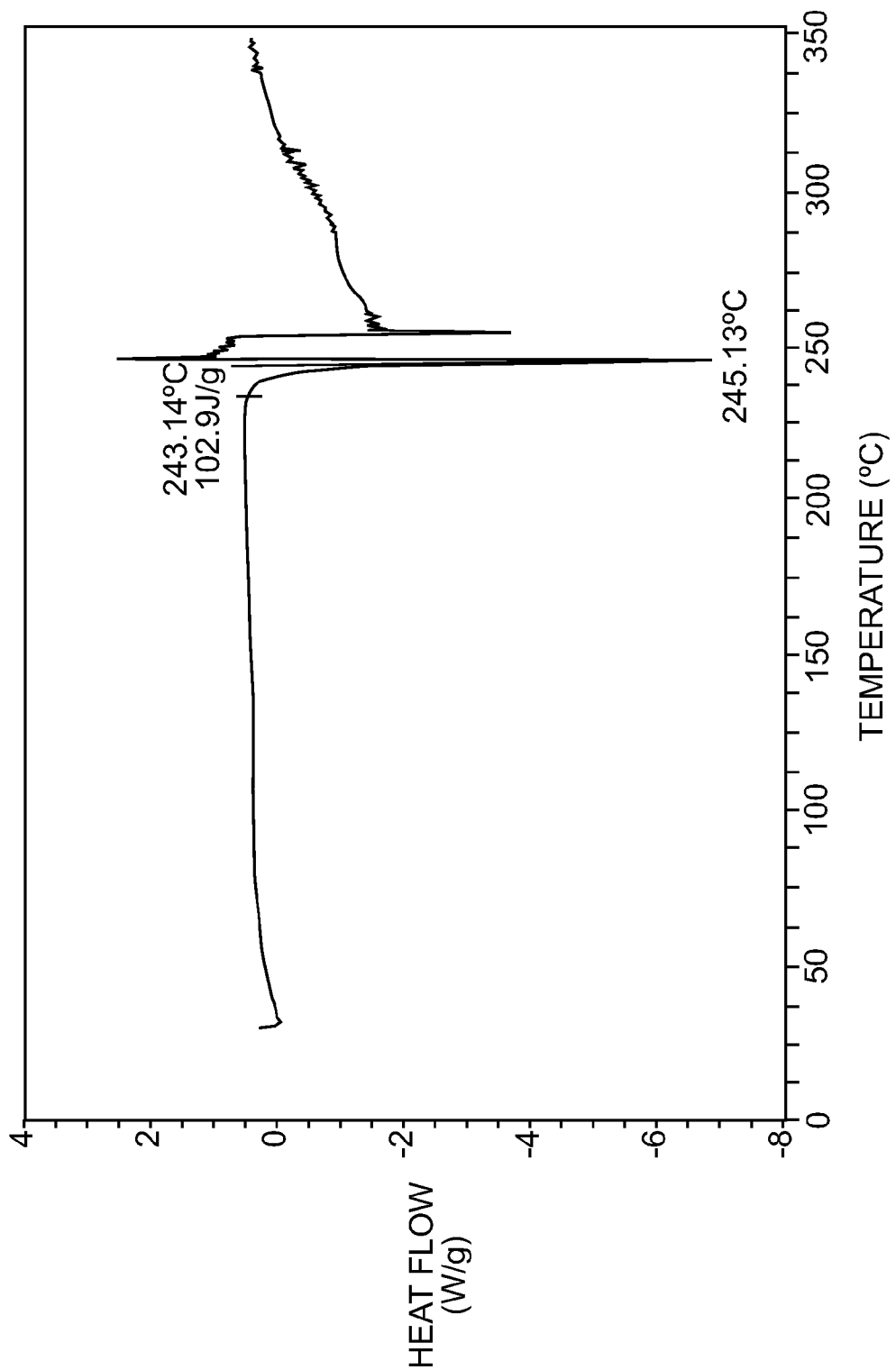
FIG. 8 is a DSC thermogram of the crystalline hydrofumarate salt of mutilin 14-(exo-8-methyl-8-azabicyclo[3.2.1]oct-3-ylsulfanyl)-acetate.
Figure 9:
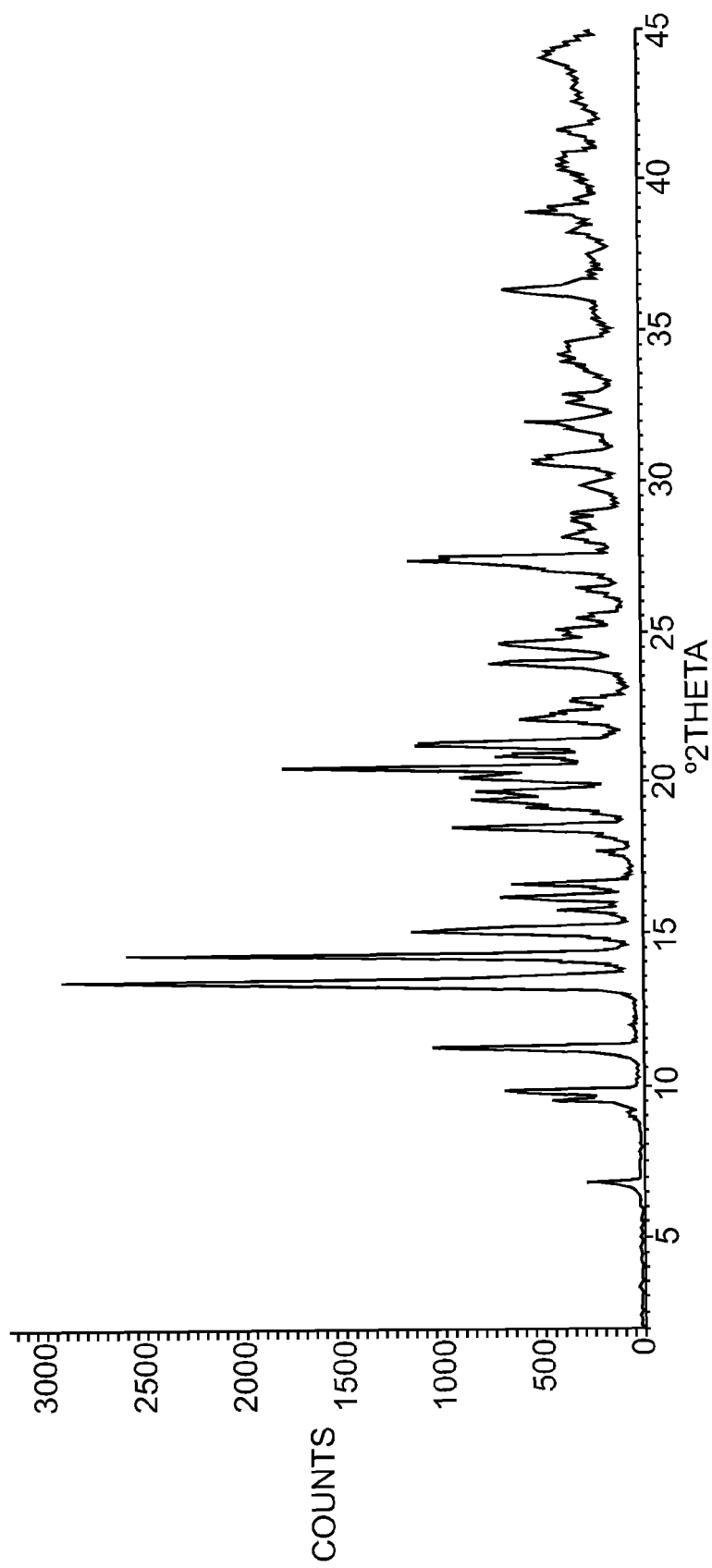
FIG. 9 is an XRPD pattern of the crystalline hydrofumarate salt of mutilin 14-(exo-8-methyl-8-azabicyclo[3.2.1]oct-3-ylsulfanyl)-acetate.
Figure 10:
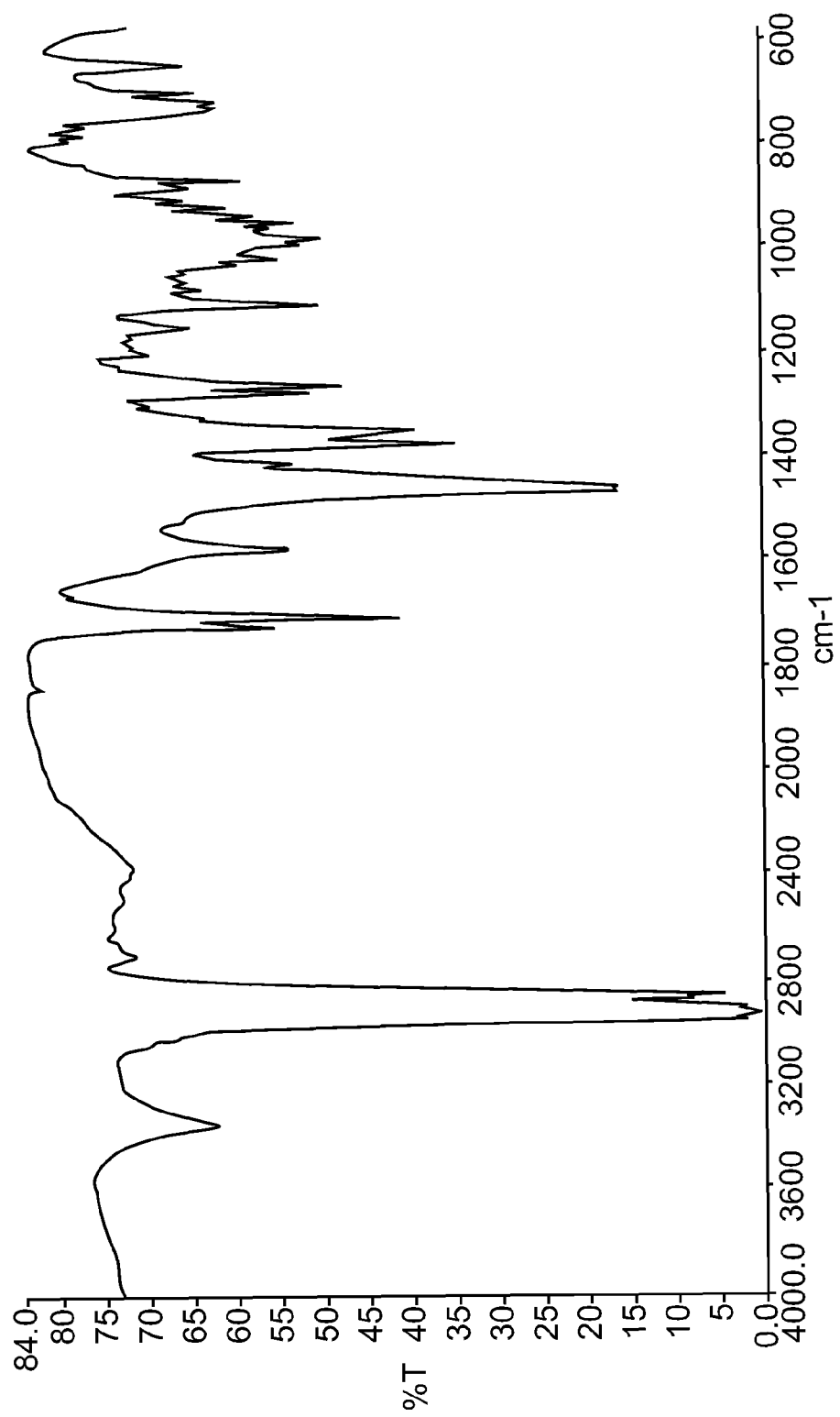
FIG. 10 is an infra-red spectrum of the crystalline hydromaleate salt of mutilin 14-(exo-8-methyl-8-azabicyclo[3.2.1]oct-3-ylsulfanyl)-acetate measured by ATR (attenuated total reflectance).
Figure 11:
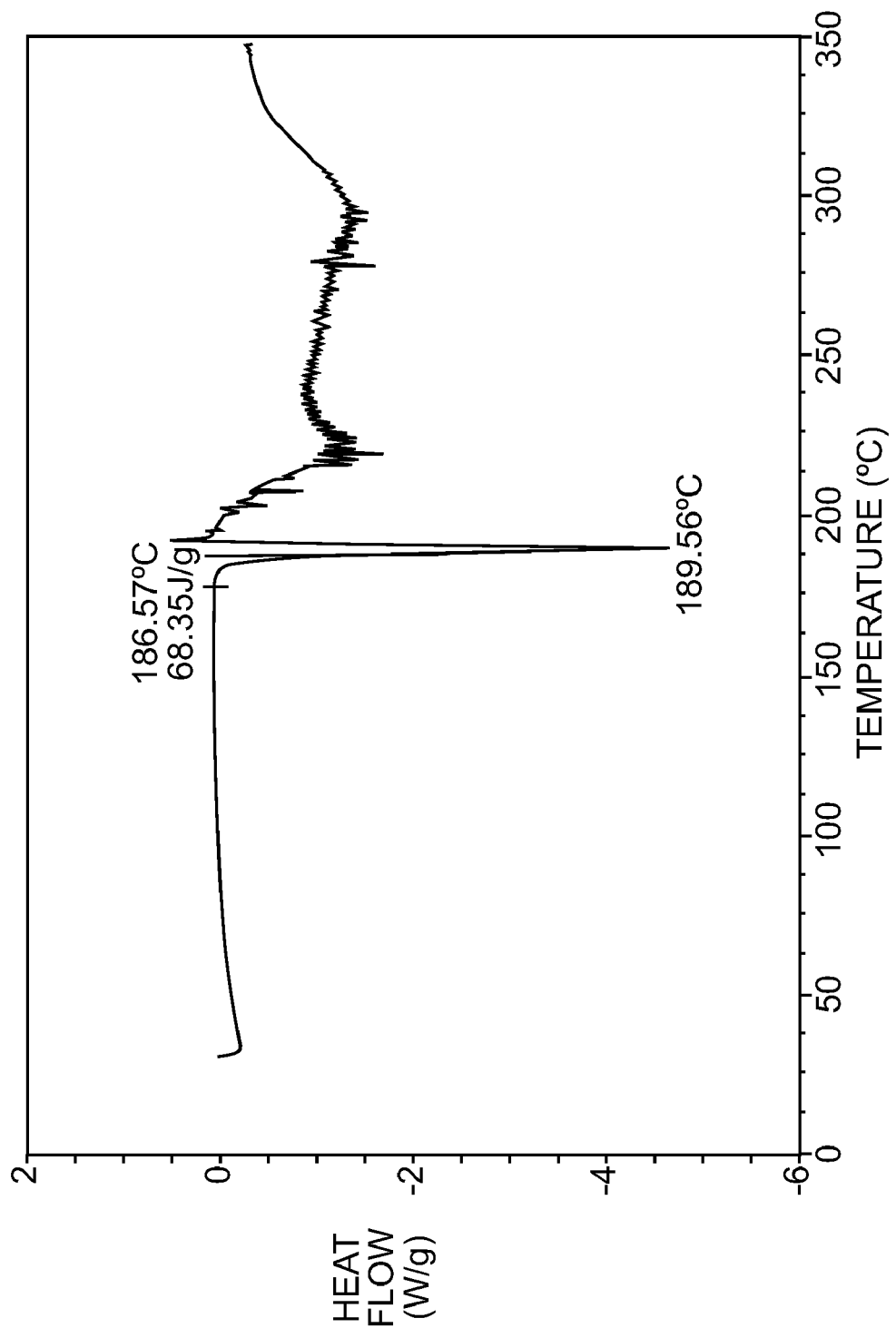
FIG. 11 is a DSC thermogram of the crystalline hydromaleate salt of mutilin 14-(exo-8-methyl-8-azabicyclo[3.2.1]oct-3-ylsulfanyl)-acetate.
Figure 12:
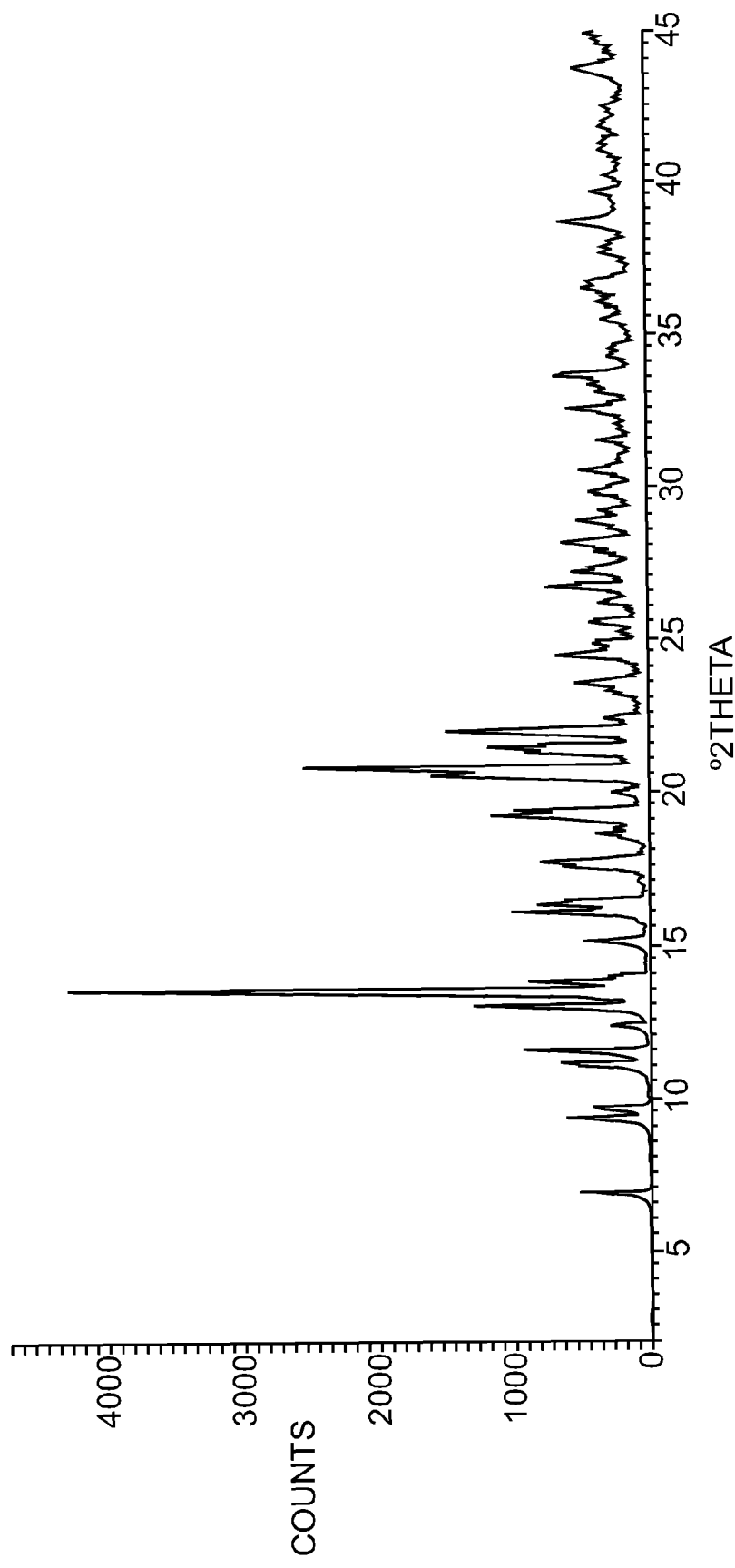
FIG. 12 is an XRPD pattern of the crystalline hydromaleate salt of mutilin 14-(exo-8-methyl-8-azabicyclo[3.2.1]oct-3-ylsulfanyl)-acetate.
Figure 13:
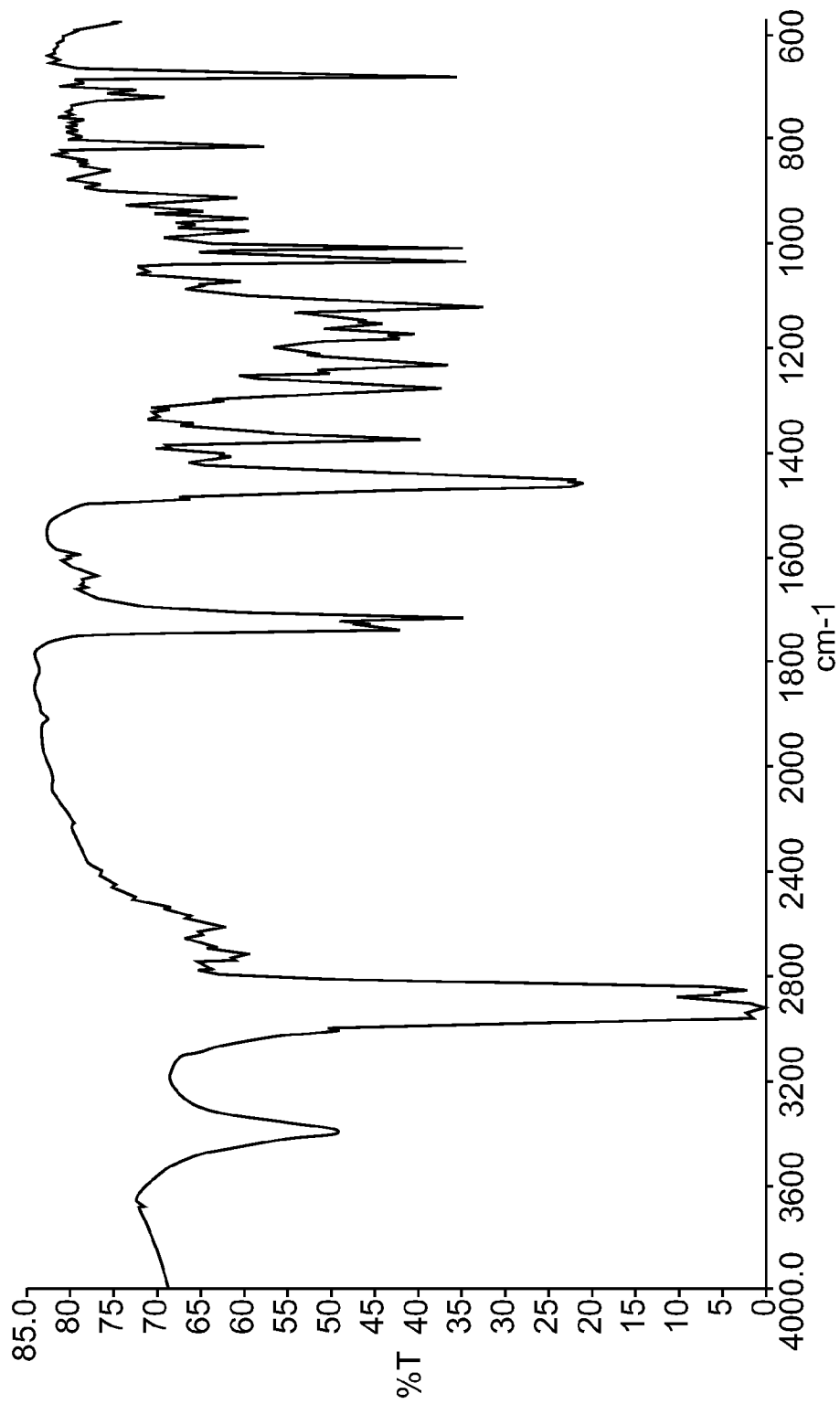
FIG. 13 is an infra-red spectrum of the crystalline tosylate salt of mutilin 14-(exo-8-methyl-8-azabicyclo[3.2.1]oct-3-ylsulfanyl)-acetate measured by ATR (attenuated total reflectance).
Figure 14:
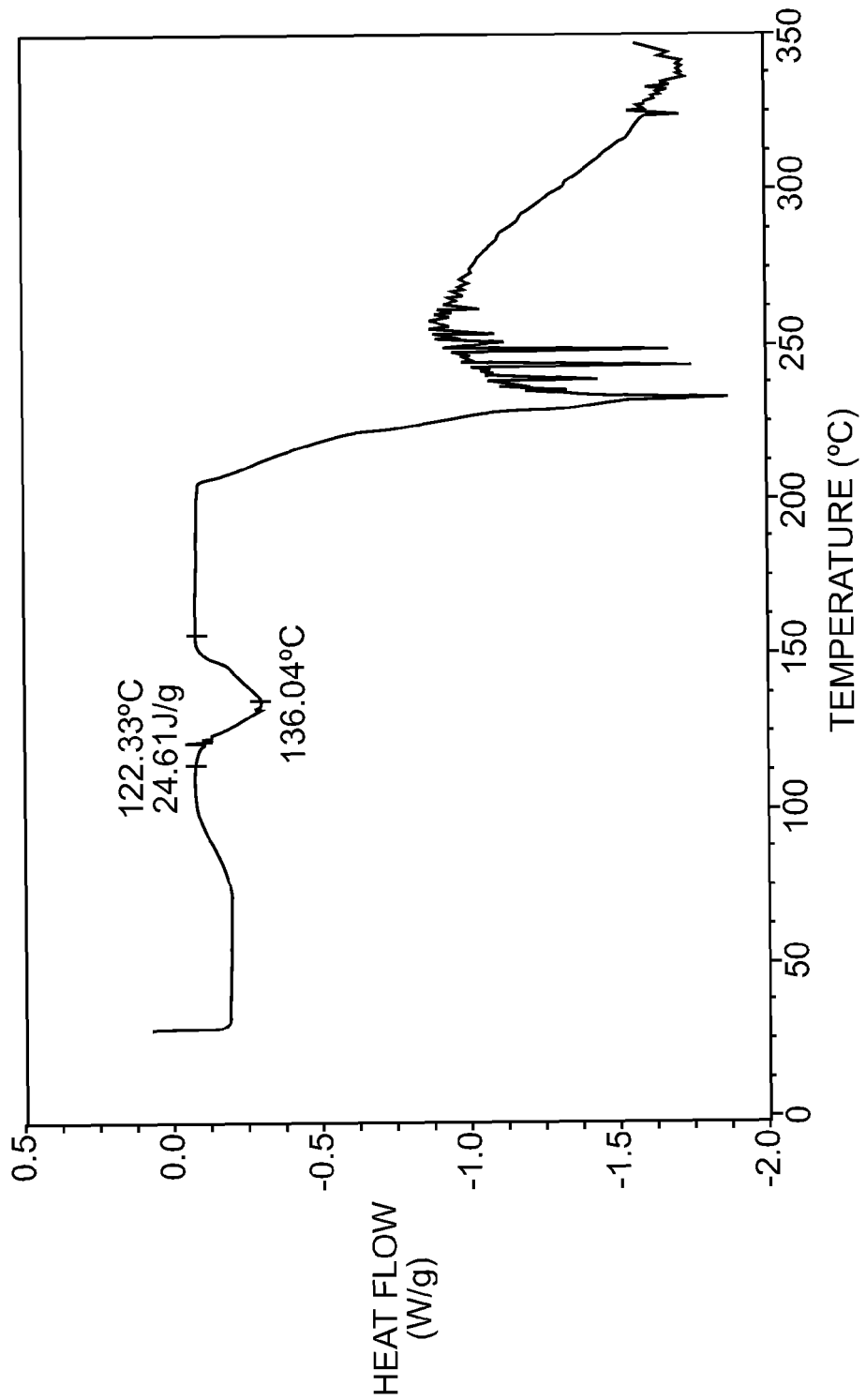
FIG. 14 is a DSC thermogram of the crystalline tosylate salt of mutilin 14-(exo-8-methyl-8-azabicyclo[3.2.1]oct-3-ylsulfanyl)-acetate.
Figure 15:
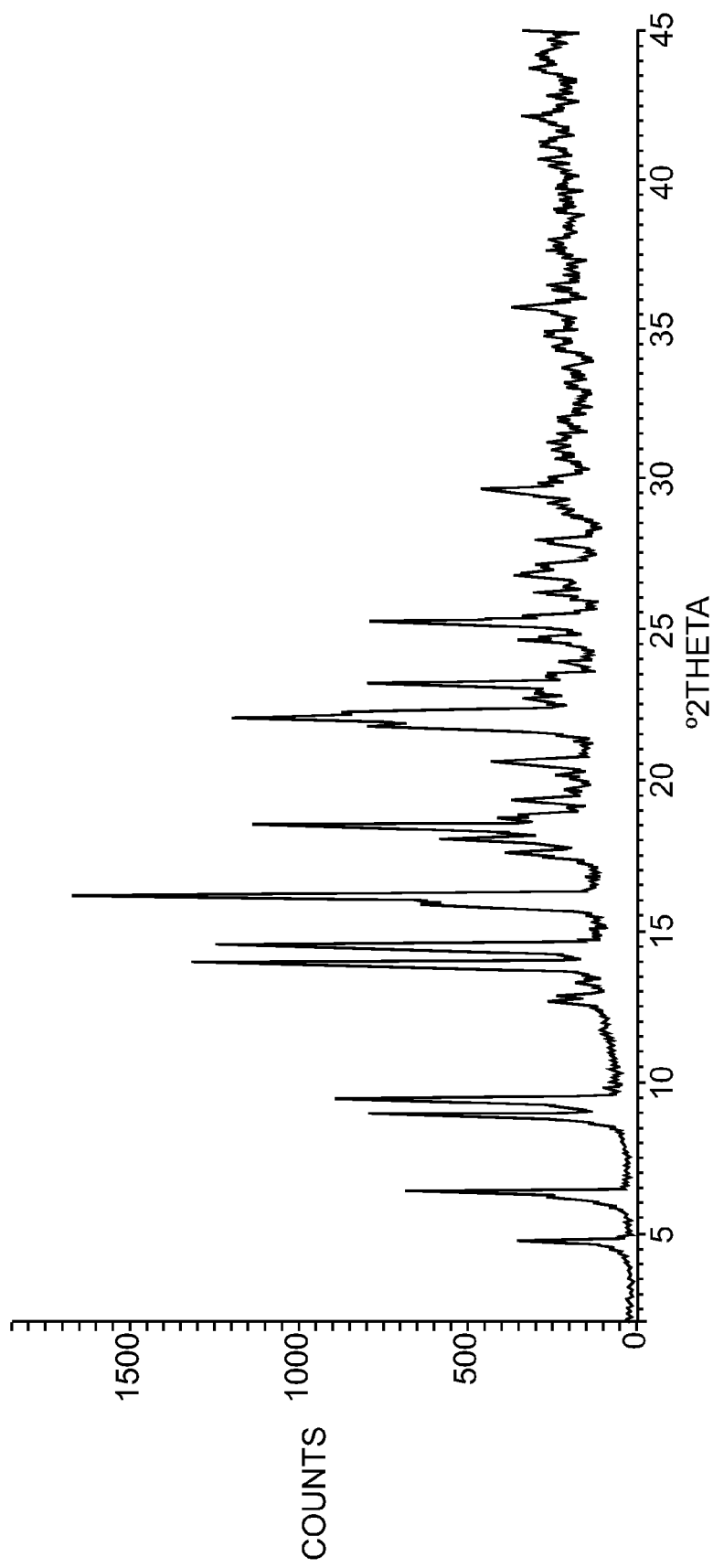
FIG. 15 is an XRPD pattern of the crystalline tosylate salt of mutilin 14-(exo-8-methyl-8-azabicyclo[3.2.1]oct-3-ylsulfanyl)-acetate.

In a further preferred embodiment the present invention provides a crystalline hydrosuccinate salt of mutilin 14-(exo-8-methyl-8-azabicyclo[3.2.1]oct-3-ylsulfanyl)-acetate characterised in that it provides an XRPD pattern substantially in accordance with FIG. 6.

The salts according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight. An impure or less pure form of a salt according to the invention may, for example, be used in the preparation of a more pure form of the same salt or of a different salt suitable for pharmaceutical use.

The salts according to the present invention may be prepared by conventional methodology.

In a further embodiment of the present invention there is provided a process for preparing a pharmaceutically acceptable salt of mutilin 14-(exo-8-methyl-8-azabicyclo[3.2.1] oct-3-ylsulfanyl)-acetate as hereinbefore defined, or a solvate thereof, which process comprises mixing a solution or suspension of the corresponding acid with a solution of mutilin 14-(exo-8-methyl-8-azabicyclo[3.2.1]oct-3-ylsulfanyl)-acetate in a suitable solvent.

Solvents suitable for use in the process according to the present invention include alcohols such as isopropanol and esters such as ethyl acetate.

In a preferred embodiment the acid and mutilin 14-(exo-8-methyl-8-azabicyclo[3.2.1]oct-3-ylsulfanyl)-acetate are dissolved separately in isopropanol, where necessary heating to from 45 to 55° C., and the solutions then mixed. The resulting mixture is typically stirred until crystallisation occurs.

Mutilin 14-(exo-8-methyl-8-azabicyclo[3.2.1]oct-3-ylsulfanyl)-acetate may be prepared by the procedures described in WO99/21855. Preferably, the mutilin 14-(exo-8-methyl-8- azabicyclo[3.2.1]oct-3-ylsulfanyl)-acetate is prepared by the process hereinbefore described.

The salts of the present invention have antimicrobial properties and are therefore of use in therapy, in particular for treating microbial infections in animals, especially mammals, including humans, in particular humans and domesticated animals (including farm animals). The salts may be used for the treatment of infections caused by, for example, Gram-positive and Gram-negative bacteria and mycoplasmas, including, for example, *Staphylococcus aureus, Staphylococcus epidermidis, Enterococcus faecalis, Streptococcus pyogenes, Streptococcus agalactiae, Streptococcus pneumoniae, Haemophilus* sp., *Neisseria* sp., *Legionella* sp., *Chlamydia* sp., *Moraxella catarrhalis, Mycoplasma pneumoniae*, and *Mycoplasma gallisepticum*.

The present invention also provides a method of treating microbial infections in animals, especially in humans and in domesticated mammals, which comprises administering a salt of the invention or a solvate thereof, or a composition comprising a salt or solvate according to the invention, to a patient in need thereof.

The invention further provides the use of a salt of the invention or a solvate thereof in the preparation of a medicament for use in the treatment of microbial infections.

Salts of the present invention may be used to treat skin and soft tissue infections, for example secondarily infected dermotoses or traumatic lesions and impetigo, and acne, by topical application. Accordingly, in another embodiment the present invention provides the use of a salt of the invention or a solvate thereof in the preparation of a medicament adapted for topical administration for use in the treatment of skin and soft tissue infections and also in the treatment of acne in humans.

It will be appreciated that reference to treatment includes acute treatment or prophylaxis as well as the alleviation of established symptoms.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

The salts according to the invention may suitably be administered to the patient at a daily dosage of from 1.0 to 50 mg/kg of body weight. For an adult human (of approximately 70 kg body weight), from 50 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

While it is possible that, for use in therapy, a salt of the present invention may be administered as the raw chemical, it is preferable to present the active ingredient as a pharmaceutical formulation e.g. when the agent is in admixture with a suitable pharmaceutical excipient, diluent or carrier selected with regard to the intended route of administration and standard pharmaceutical practice.

More specifically, the salts and compositions according to the invention may be formulated for administration in any convenient way for use in human or veterinary medicine, by analogy with other antibiotics.

Accordingly, in one embodiment the present invention provides a pharmaceutical composition or formulation comprising at least one salt of the invention or a solvate thereof in association with a pharmaceutically acceptable carrier and/or excipient. The carrier and/or excipient must be "acceptable" in the sense of being compatible with the other ingredients of the formulation and not deleterious to the recipient thereof.

In another embodiment the invention provides a pharmaceutical composition comprising, as active ingredient, at least one salt of the invention or a solvate thereof in association with a pharmaceutically acceptable carrier and/or excipient for use in therapy, and in particular, in the treatment of human or animal subjects suffering from a condition susceptible to amelioration by an antibacterial compound.

In another embodiment the invention provides a pharmaceutical composition comprising a therapeutically effective amount of the salts of the present invention or solvates thereof and a pharmaceutically acceptable excipient, diluent or carrier (including combinations thereof).

There is further provided by the present invention a process of preparing a pharmaceutical composition, which process comprises mixing at least one salt of the invention or a solvate thereof, together with a pharmaceutically acceptable excipient, diluent and/or carrier.

The pharmaceutical compositions may be for human or animal usage in human and veterinary medicine and will typically comprise any one or more of a pharmaceutically acceptable excipient, diluent or carrier. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical diluent, excipient or carrier can be selected with regard to the intended route of administration and standard pharmaceutical practice. The pharmaceutical compositions may comprise as—or in addition to—the excipient, diluent or carrier, any suitable binder(s), lubricant(s), suspending agent(s), coating agent(s), solubilising agent(s), preservative(s), stabiliser(s), dye(s), flavouring agent(s) and antioxidant(s). Examples of preservatives include sodium benzoate, sorbic acid and esters of p-hydroxybenzoic acid.

For some embodiments, the agents of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser.

Alpha-, beta- and gamma-cyclodextrins are most commonly used and suitable examples are described in WO 91/11172, WO 94/02518 and WO 98/55148.

The salts of the invention may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196 (SmithKline Beecham).

The routes for administration (delivery) include, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual. Preferably the route of administration is topical.

It is to be understood that not all of the salts need be administered by the same route. Likewise, if the composition comprises more than one active component, then those components may be administered by different routes. For example, for some applications, preferably the agent is administered orally and for other applications, preferably the agent is administered topically.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by both routes. In a preferred embodiment the agents of the present invention are delivered topically. Hence, preferably the agent is in a form that is suitable for topical delivery.

The salts and compositions according to the invention can be administered (e.g. orally or topically) in the form of tablets, capsules, powders, granules, lozenges, creams, syrups, sprays, ovules, elixirs, or liquid preparations, for example solutions or suspensions, which may be formulated for oral use or in sterile form for parenteral administration by injection or infusion and which may contain flavouring or colouring agents, for immediate-, delayed-, modified-, sustained-, pulsed- or controlled-release applications.

Compositions according to the invention intended for topical administration may, for example, be in the form of ointments, creams, lotions, solutions, dusting powders, eye ointments, eye drops, ear drops, nose drops, nasal sprays, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, ethanol or oleyl alcohol for lotions and aqueous bases for sprays. Such carriers may constitute from about 1% to about 98% by weight of the formulation; more usually they will constitute up to about 80% by weight of the formulation. For example, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Compositions according to the invention intended for topical administration, in addition to the above, may also contain a steroidal anti-inflammatory agent; for example, betamethasone.

Compositions according to the invention may also be dermally or transdermally administered, for example, by the use of a skin patch. However, preferably the compositions of the present invention are used topically to treat localised, non-systemic infections rather than systemic infections.

Compositions according to the invention may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

A salt or composition according to the invention is suitably administered to the patient in an antimicrobially effective amount.

A composition according to the invention may suitably contain from 0.001% by weight, preferably (for other than spray compositions) from 10 to 60% by weight, of a salt according to the invention (based on the total weight of the composition), depending on the method of administration.

When the compositions according to the invention are presented in unit dosage form, for instance as a tablet, each unit dose may suitably comprise from 25 to 1000 mg, preferable from 50 to 500 mg, of a salt according to the invention.

The salts of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. The compounds of the present invention may be used in combination with other antibacterial drugs such as a penicillin, a cephalosporin, a sulfonamide or an erythromycin.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

According to a third aspect of the present invention we have found that mutilin 14-(exo-8-methyl-8-azabicyclo[3.2.1]oct-3-ylsulfanyl)-acetate or a pharmaceutically acceptable salt or solvate thereof is especially suitable for topical administration, particularly to treat localised, non-systemic infections.

Thus in one embodiment the present invention provides a pharmaceutical composition for topical administration comprising mutilin 14-(exo-8-methyl-8-azabicyclo[3.2.1]oct-3-ylsulfanyl)-acetate or a pharmaceutically acceptable salt or solvate thereof, and a pharmaceutically acceptable excipient, diluent or carrier.

Suitable topical compositions are as hereinbefore defined.

Salts and solvates suitable for use in the composition according to the present invention are also as hereinbefore described. Preferably, the composition comprises mutilin 14-(exo-8-methyl-8-azabicyclo[3.2.1]oct-3-ylsulfanyl)-acetate or the hydrosuccinate salt of mutilin 14-(exo-8-methyl-8-azabicyclo[3.2.1]oct-3-ylsulfanyl)-acetate, or a solvate thereof.

In another embodiment the present invention provides a method of treating microbial infections in animals, especially in humans and in domesticated mammals, which comprises topically administering mutilin 14-(exo-8-methyl-8-azabicyclo[3.2.1]oct-3-ylsulfanyl)-acetate or a pharmaceutically acceptable salt or solvate thereof.

The invention further provides the use of mutilin 14-(exo-8-methyl-8-azabicyclo[3.2.1]oct-3-ylsulfanyl)-acetate or a pharmaceutically acceptable salt or solvate thereof in the preparation of a medicament for use in the treatment of microbial infections, which medicament is administered topically.

According to a fourth aspect of the present invention we have found pharmaceutical compositions or formulations for topical administration comprising mutilin 14-(exo-8-methyl-8-azabicyclo[3.2.1]oct-3-ylsulfanyl)-acetate or a pharmaceutically acceptable salt or solvate thereof which have advantageous cosmetic properties, are smooth rather than gritty and exhibit a sufficient release rate to exert their therapeutic effect.

Thus in one embodiment the present invention provides a pharmaceutical composition for topical administration comprising:

(a) mutilin 14-(exo-8-methyl-8-azabicyclo[3.2.1]oct-3-ylsulfanyl)-acetate or a pharmaceutically acceptable salt or solvate thereof in particulate form wherein $D_{90}$ is from 15 to 40 µm, and (b) an ointment base.

The composition according to the present invention comprises particles of mutilin 14-(exo-8-methyl-8-azabicyclo[3.2.1]oct-3-ylsulfanyl)-acetate or a pharmaceutically acceptable salt or solvate thereof. Salts and solvates suitable for use in the composition according to the present invention are as hereinbefore described. Preferably, the composition comprises particles of mutilin 14-(exo-8-methyl-8-azabicyclo[3.2.1]oct-3-ylsulfanyl)-acetate or the hydrosuccinate salt of mutilin 14-(exo-8-methyl-8-azabicyclo[3.2.1]oct-3-ylsulfanyl)-acetate, or a solvate thereof.

When used herein, the term "$D_{90}$" refers to the particle diameter which 90% of the particles are less than. Preferably, $D_{90}$ of the particles in the composition according to the present invention is from 15 to 25 µm.

In a preferred embodiment the particles in the composition according to the present invention also have a $D_{50}$ of from 5 to 15 µm. When used herein, the term "$D_{50}$" refers to the median particle diameter.

Methods for measuring particle diameter distribution are well known. Preferably, the particle diameter distribution of the particles in the composition according to the present invention are measured using a laser diffraction technique. Suitable laser diffraction apparatus include, for example, the Sympatec HELOS/QUIXEL, obtainable from Sympatec UK and Ireland, Bury Business Centre, Kay Street, Bury BL9 6BU, United Kingdom, email: sympatec.uk@btinternet.com, or the Malvern Mastersizer obtainable from Malvern Instruments, Malvern, UK. A general description of measuring particle diameter distribution by laser diffraction can be found in Physical Characterization of Pharmaceutical Solids, Drugs and Pharmaceutical Sciences, Volume 70, pages 175 to 178.

Ointment bases suitable for use in the compositions according to the present invention are known in the art and include, for example, White Petrolatum USP, Hydrophilic Petrolatum USP, Anhydrous Lanolin USP, Lanolin USP, Hydrous lanolin USP, Aquaphor® (a registered trademark of Beiersdorf), Eucerin® (a registered trademark of Beiersdorf), ACTIBASE® (a registered trademark of Sante) and Polyethylene Glycol Ointment USP. Preferably, the ointment base is petrolatum, see for instance the Handbook of Pharmaceutical Excipients, Fourth Edition, Edited by R. C. Rowe, P. J. Sheskey and P. J. Weller, Published by Pharmaceutical Press and the American Pharmaceutical Association, page 421 to 423, in particular White Petrolatum USP.

The compositions according to the invention typically contain up to 5% w/w of particles in the ointment base, preferably from 0.5 to 2% w/w, more preferably 0.5 to 1% w/w and most preferably about 1% w/w.

In another embodiment the present invention provides a process for preparing a pharmaceutical composition for topical administration as hereinbefore defined comprising mixing (a) mutilin 14-(exo-8-methyl-8-azabicyclo[3.2.1]oct-3-ylsulfanyl)-acetate or a pharmaceutically acceptable salt or solvate thereof in particulate form wherein $D_{90}$ is from 15 to 40 µm, and (b) an ointment base.

When petrolatum is used as the ointment base, the petrolatum is preferably heated to a temperature of from 60 to 70° C. before mixing.

Mutilin 14-(exo-8-methyl-8-azabicyclo[3.2.1]oct-3-ylsulfanyl)-acetate may be prepared by the procedures described in WO99/21855. Preferably, the mutilin 14-(exo-8-methyl-8-azabicyclo[3.2.1]oct-3-ylsulfanyl)-acetate is prepared by the process hereinbefore described. The pharmaceutically acceptable salts and solvates of mutilin 14-(exo-8-methyl-8-azabicyclo[3.2.1]oct-3-ylsulfanyl)-acetate are also preferably as hereinbefore described.

Particles of mutilin 14-(exo-8-methyl-8-azabicyclo[3.2.1]oct-3-ylsulfanyl)-acetate or a pharmaceutically acceptable salt or solvate thereof may be prepared by, for example, milling using known milling procedures to obtain a particle size appropriate for use in the compositions according to the present invention. Mill types suitable for use according to the present invention are known in the art and include, for example, classifier mills (ZPS Mill, Alpine), fluid bed air jet mills (AFG Mill, Alpine), spiral air jet mills (AS Mill, Alpine) and high speed impact mills (USP Mill, Alpine).

The compositions of the present invention have antimicrobial properties and are therefore of use in therapy, in particular for treating microbial infections in animals, especially mammals, including humans, in particular humans and domesticated animals (including farm animals). The compositions may be used for the treatment of infections caused by, for example, Gram-positive and Gram-negative bacteria and mycoplasmas, including, for example, *Staphylococcus aureus, Staphylococcus epidermidis, Enterococcus faecalis, Streptococcus pyogenes, Streptococcus agalactiae, Streptococcus pneumoniae, Haemophilus* sp., *Neisseria* sp., *Legionella* sp., *Chlamydia* sp., *Moraxella catarrhalis, Mycoplasma pneumoniae,* and *Mycoplasma gallisepticum.*

The present invention also provides a method of treating microbial infections in animals, especially in humans and in domesticated mammals, which comprises administering a composition of the invention to a patient in need thereof.

The invention further provides the use of a composition of the invention in the preparation of a medicament for use in the treatment of microbial infections.

Compositions of the present invention may be used to treat skin and soft tissue infections, for example secondarily infected dermotoses or traumatic lesions and impetigo, and acne, by topical application. Accordingly, in another embodiment the present invention provides the use of a composition of the invention in the preparation of a medicament adapted for topical administration for use in the treatment of skin and soft tissue infections and also in the treatment of acne in humans.

According to a fifth aspect of the present invention we have found that mutilin 14-(exo-8-methyl-8-azabicyclo[3.2.1]oct-3-ylsulfanyl)-acetate or a pharmaceutically acceptable salt or solvate thereof may be administered twice daily (bid).

Thus in one embodiment the present invention provides a method of treating microbial infections in animals, especially in humans and in domesticated mammals, which comprises administering mutilin 14-(exo-8-methyl-8-azabicyclo[3.2.1]oct-3-ylsulfanyl)-acetate or a pharmaceutically acceptable salt or solvate thereof bid.

The invention further provides the use of mutilin 14-(exo-8-methyl-8-azabicyclo[3.2.1]oct-3-ylsulfanyl)-acetate or a pharmaceutically acceptable salt or solvate thereof in the preparation of a medicament for use in the treatment of microbial infections, which medicament is administered bid.

Suitably, the bid administration is at 12 hour intervals, although a greater or lesser interval between administrations may be used.

Preferably, the mutilin 14-(exo-8-methyl-8-azabicyclo[3.2.1]oct-3-ylsulfanyl)-acetate or a pharmaceutically acceptable salt or solvate thereof is administered topically in the form of a pharmaceutical composition as hereinbefore defined.

Salts and solvates suitable for use according to the present invention are as hereinbefore described. Preferably, the mutilin 14-(exo-8-methyl-8-azabicyclo[3.2.1]oct-3-ylsulfanyl)-acetate is in the form of the free base or the hydrosuccinate salt, or a solvate thereof.

According to a sixth aspect of the present invention we have found that use of mutilin 14-(exo-8-methyl-8-azabicyclo[3.2.1]oct-3-ylsulfanyl)-acetate or a pharmaceutically acceptable salt or solvate thereof may allow the duration of therapy to be reduced as compared with conventional antibacterial therapy.

Thus in one embodiment the present invention provides a method of treating microbial infections in animals, especially in humans and in domesticated mammals, which comprises administering mutilin 14-(exo-8-methyl-8-azabicyclo[3.2.1]oct-3-ylsulfanyl)-acetate or a pharmaceutically acceptable salt or solvate thereof for 5 to 7 days.

The invention further provides the use of mutilin 14-(exo-8-methyl-8-azabicyclo[3.2.1]oct-3-ylsulfanyl)-acetate or a pharmaceutically acceptable salt or solvate thereof in the preparation of a medicament for use in the treatment of microbial infections, which medicament is administered for 5 to 7 days.

Preferably, the mutilin 14-(exo-8-methyl-8-azabicyclo[3.2.1]oct-3-ylsulfanyl)-acetate or a pharmaceutically acceptable salt or solvate thereof is administered topically in the form of a pharmaceutical composition as hereinbefore defined.

Salts and solvates suitable for use according to the present invention are as hereinbefore described. Preferably, the mutilin 14-(exo-8-methyl-8-azabicyclo[3.2.1]oct-3-ylsulfanyl)-acetate is in the form of the free base or the hydrosuccinate salt, or a solvate thereof.

The invention is illustrated by the following Examples.

EXAMPLES

The infra-red spectra, XRPD patterns and DSC profiles described herein may be recorded using techniques well known to those skilled in the art. For example, the infra-red spectra, XRPD patterns and DSC profiles may be recorded as follows:

IR Spectroscopy

The infra-red spectrum of the solid product was recorded using a Perkin Elmer Spectrum One FT-IR spectrometer fitted with a Diamond/ZnSe Universal ATR Accessory at 2 $cm^{-1}$ resolution. Data were digitised at 1 $cm^{-1}$ intervals.

When indicated herein that a compound has a peak in its infra-red spectrum at a given value, it typically means that the peak is within ±2 $cm^{-1}$.

XRPD

The X-ray powder diffractogram pattern of the product was recorded on a Philips X'Pert Pro, Model PW3040/60 using the following acquisition conditions: Tube anode: Cu, K alpha 1 and K alpha 2 radiation, Generator tension: 40 kV, Generator current: 45 mA, Start angle: 2.0 degrees 2 theta, End angle: 45.0 degrees 2 theta, Step size: 0.02 degrees 2 theta, time per step: 4.0 seconds.

When indicated herein that a compound has a peak in its XRPD pattern at a given value, it typically means that the peak is within ±0.1.

DSC

The DSC thermogram of the product was obtained using a TA Instruments Q1000 calorimeter. The sample was weighed into an aluminium pan, a pan lid placed on top and lightly crimped without sealing the pan. The experiment was conducted using a heating rate of 10° C. $min^{-1}$.

When indicated herein that a compound has a peak in its DSC profile at a given value, it typically means that the peak is within ±2° C.

Note on Naming of Pleuromutilin Analogues

In the Examples, compound (a), which in the IUPAC system has the systematic name (1S,2R,3S,4S,6R,7R,8R,14R)-3,6-dihydroxy-2,4,7,14-tetramethyl-4-vinyl-tricyclo[5.4.3.0$^{1,8}$]tetradecan-9-one, is referred to using the trivial name mutilin and with the numbering system described by H Berner, G Schulz, and H Schneider in *Tetrahedron*, 1981, 37, 915-919.

(a)

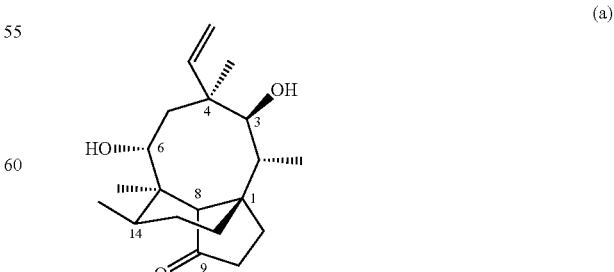

IUPAC numbering

25
-continued

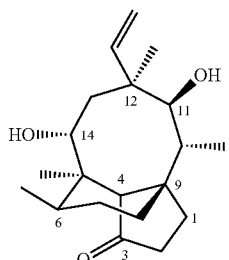

(a)

Mutilin numbering

Likewise, compound (b), which has the systematic name (1R,2R,4S,6R,7R,8S,9R,14R)-6-hydroxy-9-methoxy-2,4,7,14-tetramethyl-4-vinyl-tricyclo[5.4.3.0$^{1,8}$]tetradecan-3-one, is named as (3R)-3-deoxo-11-deoxy-3-methoxy-11-oxo-4-epi-mutilin.

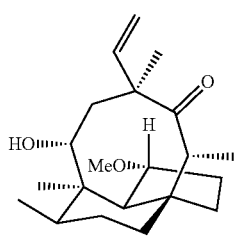

(b)

Reference Example 1

Mutilin 14-(exo-8-methyl-8-azabicyclo[3.2.1]oct-3-ylsulfanyl)-acetate

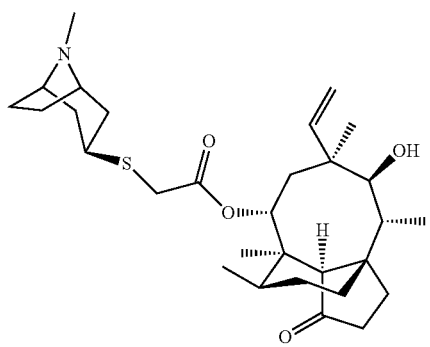

The title compound was prepared from endo-8-methyl-8-azabicyclo[3.2.1]octan-3-ol and mutilin 14-methanesulfonyloxyacetate using the process described in Example 15 of WO99/21855 (0.09 g, 17%); $^1$H NMR (CDCl$_3$) inter alia 0.74 (3H, d, J=6.7 Hz), 0.99 (3H, d, J=7.5 Hz), 1.18 (3H, s), 1.63 (3H, s), 2.28 (3H, s), 3.0 (1H, m), 3.13 (2H, s), 3.16 (2H, m), 3.36 (1H, m), 5.15 to 5.37 (2H, m), 5.77 (1H, d, J=8.3 Hz), 6.49 (1H, m); MS (+ve ion electrospray) m/z 518 (MH$^+$, 100%).

Reference Example 2

Mutilin 14-(exo-8-methyl-8-azabicyclo[3.2.1]oct-3-ylsulfanyl)-acetate

22-Deoxy-22-sulfanylpleuromutilin (U.S. Pat. No. 4,130,709, 1978) (0.1 g, 0.00025 mole) in ethanol (4 ml) was treated with sodium methoxide (0.014 g, 0.0026 mole) and the resulting mixture stirred for 30 minutes. A solution of endo-3-methanesulfonyloxy-8-methyl-8-azabicyclo[3.2.1]octane (prepared from endo-8-methyl-8-azabicyclo[3.2.1]octan-3-ol and methanesulfonyl chloride) (0.061 g, 0.00028 mole) in ethanol (1 ml) was then added. Stirring was continued for 68 hours; a further portion of endo-3-methanesulfonyloxy-8-methyl-8-azabicyclo[3.2.1]octane (0.061 g, 0.00028 mole) was then added and stirring continued for a further 18 hours. The mixture was then diluted with dichloromethane, washed twice with aqueous potassium carbonate, once with brine, dried over magnesium sulfate and concentrated in vacuo. Chromatography on silica gel eluting with chloroform/methanol/35% ammonia solution (9:1:0:1) gave the title compound 0.035 g (27%), identical to the compound described in Reference Example 1.

(A) Process

It will be appreciated that, unless otherwise indicated, in the following examples each of the intermediates and final compounds may be prepared by any of the alternative procedures described.

Example 1A

Mutilin 14-(exo-8-methyl-8-azabicyclo[3.2.1]oct-3-ylsulfanyl)-acetate

Step 1a—Preparation of pleuromutilin-22-mesylate

Pleuromutilin (222.0 g, 0.59 mol) was dissolved in dichloromethane (2.25 L) under nitrogen and triethylamine (92 mL, 66.45 g, 0.66 mol) was added at ambient temperature over 15 min, during which time a slight exotherm (16.5 to 18.5° C.) was observed. After stirring for 30 min the solution was cooled to −15° C. over 20 min. A solution of methane sulphonyl chloride (52 mL, 77.5 g, 0.68 mol) in dichloromethane (430 mL) was added over 1.28 h at −9 to −15° C. The mixture was left to stir in the ice/salt bath at ~−9° C. initially. The mixture was stirred for a total of 1.5 h during which time it warmed up to 1° C. Deionized water (1.15 L) was added slowly while maintaining the temperature below 12° C. The mixture was stirred for 20 min and the phases separated. The dichloromethane phase (wt=3.70 kg) containing the title compound (267.8 g at 100% yield) was used directly in Step 5a.

Step 1b—Alternative preparation of pleuromutilin-22-mesylate

Pleuromutilin (69.95 g at 90% purity) and triethylamine (26 mL, 18.33 g) in dichloromethane (0.55 L) were cooled to −10° C. Methane sulphonyl chloride (14.5 mL, 20.87 g) in dichloromethane (0.12 L) was added over 0.5 h at −5 to −10° C. After 0.5 h the mixture was warmed to 15-20° C. and water (0.25 L) added. The phases were separated and the aqueous phase was further extracted with dichloromethane (0.06 L). The combined dichloromethane solution was concentrated by distillation collecting 0.5 L. The distillation was continued by slowly adding propan-2-ol (0.3 L) and collecting a further 0.3 L to reach a solution temperature of 78° C. n-Heptane (0.29 L) was added slowly whilst maintaining the temperature between 75-80° C. The solution became turbid with the product crystallizing. The mixture was cooled to 0° C. and stirred for 1 h. The product was filtered off, washed with chilled 2:1 n-heptane/propan-2-ol (0.075 L) and dried under vacuum to give the title compound (75.33 g, 95.6%).

Step 1c—Alternative preparation of pleuromutilin-22-mesylate

Pleuromutilin (20.1 g) and triethylamine (6.86 g) in methylisobutyl ketone (0.21 L) were cooled to −10° C. Methane sulphonyl chloride (7.91 g) in methylisobutyl ketone (0.04 L) was added at −5 to −10° C. After 1 h water (0.12 L) was added and the mixture was warmed to 20-22° C. The phases were separated and the methylisobutyl ketone phase was washed successively with water (0.09 L) and 10% brine (0.05 L). The methylisobutyl ketone solution was concentrated by distillation under reduced pressure to leave a residue of 57.4 g. Heptane (0.06 L) was added to the residue at 76-78° C. to crystallize the title compound. Further heptane (0.04 L) was added, the mixture was cooled to −5 to −8° C. and stirred for 1 h. The title compound was filtered off, washed with chilled heptane/methylisobutyl ketone (3:1, 0.028 L) and dried at <40° C. to give 21.94 g, 90.5% yield.

Step 2a—Preparation of tropine-3-mesylate

Tropine (500 g, 3.54 mol) and triethylamine (590 mL, 430 g, 4.25 mol) were mixed in dichloromethane (10 L) and cooled to <−5° C. under a stream of nitrogen. A solution of methane sulphonyl chloride (329 mL, 487 g, 4.25 mol) in dichloromethane (2 L) was added over 4.33 h between −10.4 and −4.9° C. The mixture was stirred for 15 min, the cooling bath removed, and potassium carbonate solution (2.5 L, GB98596-043)) and deionised water (1.25 L) were added. The additions took 4 min and caused an exotherm raising the temperature to 2.8° C. The mixture was warmed to 15 to 20° C., filtered and the phases allowed to separate. The aqueous phase was extracted further with dichloromethane (2.5 L). The combined organic phases were heated to distil off dichloromethane at atmospheric pressure; 10 L were collected over 1.75 h reaching a base temp. of 42.8° C. and vapour temperature of 42° C. Hexane (7.5 L) was added and after allowing the mixture to cool (overnight) the mixture was filtered and the filtrate returned to a clean flask. The solution was reheated to distil at atmospheric pressure; 7.5 L were collected up to base and vapour temperatures of 60.5 and 62° C. respectively. The mixture was cooled to 0 to 5° C., stirred for 1 h, the product filtered off and washed with hexane (1.5 L). The product was dried under vacuum in a dessicator. Crystallisation from ethyl acetate/hexane or dichloromethane/hexane gave crystalline title compound which was then used in Step 3.

Step 2b—Alternative preparation of tropine-3-mesylate

Tropine (50 g) and triethylamine (60 mL, 43.56 g) in dichloromethane (1 L) were cooled to −10° C. Methane sulphonyl chloride (36 mL, 53.28 g) in dichloromethane (0.2 L) was added over 1 h at −5+/−2° C. After 0.5 h a solution of potassium carbonate (150 g) in water (0.4 L) was added and the mixture warmed to 20° C. The phases were separated and the aqueous phase extracted with further dichloromethane (1×0.2 L). The combined dichloromethane solution was concentrated by distillation collecting 1 L. n-Heptane (0.875 L) was added and the mixture stirred for 0.5 h. The solution was decanted off and then concentrated by distillation at 610 to 650 mbar until a solution temperature of 63° C. was reached. The solution was cooled to 0° C. with crystallization occurring during the cooling. The mixture was stirred for 1 h, the product isolated by filtration, washed and dried at <30° C. to give the title compound (60.62 g, 78.1%).

Step 2c—Alternative preparation of tropine-3-mesylate

Tropine (50 g) and diisopropylethylamine (48.05 g) in dichloromethane (0.5 L) were cooled to −10° C. Methane sulphonyl chloride (44.7 g) in dichloromethane (0.125 L) was added over 0.75 h at <−5° C. After 0.5 h a solution of potassium carbonate (75 g) in water (0.2 L) was added and the mixture warmed to 20° C. The phases were separated and the dichloromethane solution concentrated by distillation under reduced pressure at <20° C. to leave a residue whereby the dichloromethane content was 51% w/w. Heptane (0.05 L) was added and the solution cooled to 0° C. to crystallize the title compound. Further heptane (0.45 L) was added and the mixture kept under vacuum (350 mbar) at 20-25° C. until the dichloromethane content was 8% w/w. The mixture was cooled to 0° C. and stirred for 1 h. The product was isolated by filtration, washed and dried at <30° C. to give the title compound (68.5 g, 88.1%).

Step 3a—Preparation of tropine-3-xanthate

Tropine-3-mesylate (243.6 g, 1.11 mol) and sodium ethylxanthate (245.1 g, 1.70 mol) were added to stirred toluene (1.25 L) at 36° C. under nitrogen. The mixture was reheated to 35-37° C. (from 30° C.) where it was maintained overnight (~18 h). The oilbath was removed and water (500 mL) added. After 2 h stirring the mixture was filtered and the phases separated. The toluene phase was washed with deionised water (1×500 mL, 1×300 mL). The yield was found to be 192.36 g, 70.6%, based on 14.42% w/w in solution, by LC analysis against a reference standard. The solution was stored at 4° C. prior to use in Step 4a.

Step 3b—Alternative Preparation of tropine-3-xanthate

Tropine-3-mesylate (25 g, 0.114 mol) and sodium ethylxanthate (19.7 g, 0.137 mol) were added to stirred toluene (0.075 L) under nitrogen. The stirred mixture was maintained at 30° C. for 6 h. Water (0.05 L) was added and after 15 min stirring the phases were separated. The toluene phase, containing the title compound, was used directly in the preparation of tropine-3-thiol as in Step 4b.

Step 4a—Preparation of tropine-3-thiol

The toluene solution of xanthate (Step 3a) and a solution of sodium hydroxide (94.88 g, 2.37 mol) in ethanol (950 mL) were mixed and heated to 32-33° C. over 30 min. Samples were taken periodically for analysis by LC and LC/MS; after 4 h the reaction was found to be complete (with respect to the disappearance of xanthate). The mixture was cooled to 25° C. and the initial pH of >12.8 was adjusted to <1 by the addition of 2M HCl; the addition over 1 h was mildly exothermic (24 to 28° C.). The phases were separated and the aqueous phase (2.87 L, 2.83 kg) subjected to distillation under reduced pressure (Buchi rotary evaporator); 1.4 L was removed using an Edwards pump and a bath temperature of 35-37° C. The residual solution of the title compound was stored at 4° C. prior to use in Step 5a.

Step 4b—Alternative Preparation of tropine-3-thiol

The toluene solution of xanthate (Step 3b), sodium hydroxide (11.17 g, 0.279 mol) and ethanol (0.05 L) were heated at 30° C. for 6 h. The mixture was cooled to 25° C. and the pH was adjusted to <1.5 by the addition of 4M HCl (0.095 L required). The phases were separated and the aqueous phase subjected to distillation under reduced pressure to leave a volume of ~0.09 L. The residual solution of the title compound was stored at 4° C. prior to use as in Step 5d.

Step 5a—Preparation of crude Mutilin 14-(exo-8-methyl-8-azabicyclo[3.2.1]oct-3-ylsulfanyl)-acetate The aqueous solution of thiol (Step 4a), the dichloromethane solution of mesylate (Step 1a) and tetra-n-butylammonium chloride (10.59 g, 38.1 mmol) were mixed under nitrogen (the temperature after mixing was 15° C.). The pH was adjusted to 13.05 by the addition of 980 mL of a sodium hydroxide solution (made up from 140 g in 1.75 L of water); during the addition time of 1 h the temperature was maintained at 15° C. The mixture was stirred at 12 to 15° C. and after 40 min, 1 and 2 h further portions of sodium hydroxide solution were added to adjust the pH from ~12.7 to 13.05. LC analysis after 2 h showed 0.6% (PAR) residual mesylate. The mixture was stirred for a further 1.58 h, the phases separated and water (2 L) was added to the dichloromethane solution (the pH of the resultant aqueous phase was 11.75). The pH was adjusted to 6.29 by the addition of 1M HCl (490 mL). The phases were separated and the dichloromethane solution washed by stirring (15 min) with 2 L of saturated sodium bicarbonate solution (made up from 200.g in 2 L deionised water). After separation the dichloromethane solution (2.88 kg) was concentrated using a Buchi rotary evaporator (bath temperature 34-36° C.) to leave a yellow foam residue of 307.26 g.

Step 5b—Alternative preparation of crude Mutilin 14-(exo-8-methyl-8-azabicyclo[3.2.1]oct-3-ylsulfanyl)-acetate Pleuromutilin-22-mesylate (11 g, 24.09 mMol) and n-Bu$_4$NHSO$_4$ (360.3 mg, 1.3 mMol) in MIBK (130 mL) and tropine-3-thiol in HCl (6.3% w/w, 73.9 g, ~4.65 g tropine-3-thiol, 29.58 mMol) were mixed at 20-22° C. under nitrogen. The pH (~1) of the stirred mixture was adjusted to 12.8 by the addition of 2M NaOH solution (37 mL) over approximately 20 min. The pH was re-adjusted 1 h later from 12.4 to 12.8 by the addition of 2M NaOH (1 mL) the reaction was followed by chromatography until complete. The aqueous phase was separated and discarded. Water (60 mL) was added and the pH adjusted to 7.3 to 7.5 (from 11.4) by the addition of 2M HCl (9.5 mL). The aqueous phase was separated and discarded. Water (60 mL) was added and the pH adjusted to 1.25 by the addition of 2M HCl (13 mL). After separation, the pH of the lower aqueous phase was adjusted to 7.25 using 12 mL of 2M NaOH, at which point the mixture became cloudy and on seeding crystallization occurred. After 20 min stirring, further 2M NaOH was added to adjust the pH to 9.5 to 10 to precipitate the remaining product. After 30 min stirring the product was isolated by filtration, washed with water (25 mL) and dried (10.8 g, 86.6% by weight).

Step 5c—Alternative preparation of crude Mutilin 14-(exo-8-methyl-8-azabicyclo[3.2.1]oct-3-ylsulfanyl)-acetate Pleuromutilin-22-mesylate (40 g) and tetra-butylammonium hydrogensulfate (1.4 g) were dissolved in methyl-iso-butyl ketone (200 mL) at 20-25° C. Tropine-3-thiol (hydrochloride salt) (20.36 g @ 100%) was added as an aqueous solution. The pH was adjusted to 13-13.5 using 4M sodium hydroxide solution (~100 mL) and the mixture stirred until the reaction was complete. The aqueous phase was discarded and water (100 mL) added. The pH was adjusted to 8.3±0.2 by the addition of 4M hydrochloric acid solution (~11 mL). The aqueous phase was discarded, further water (200 mL) added and the pH adjusted to <4 by the addition of 4M hydrochloric acid solution (~25 mL). The MIBK phase was discarded and the pH of the aqueous phase was adjusted to 7.5 by the addition of 4M sodium hydroxide. A seed of mutilin 14-(exo-8-methyl-8-azabicyclo[3.2.1]oct-3-ylsulfanyl)-acetate (40 mg) was added and the mixture stirred until crystallization occurred (typically <30 min). Further 4M sodium hydroxide solution (a total of 26 mL was used for both adjustments) was added over 1 h. The slurry was stirred for 1 h, the product isolated, washed with water (80 mL) and dried under vacuum (50° C.) to give 44.83 g of mutilin 14-(exo-8-methyl-8-azabicyclo[3.2.1]oct-3-ylsulfanyl)-acetate (assay of 92.9%, yield from pleuromutilin-22-mesylate of 92.0%).

Step 5d—Alternative preparation of crude Mutilin 14-(exo-8-methyl-8-azabicyclo[3.2.1]oct-3-ylsulfanyl)-acetate Pleuromutilin-22-mesylate (50 g) and tetra-butylammonium hydrogensulfate (1.75 g) were dissolved in methyl-iso-butyl ketone (250 mL) at 20-25° C. Tropine-3-thiol (hydrochloride salt) (28.65 g @ 100%), prepared as in Step 4b, was added as an aqueous solution. The pH was adjusted to 13-13.5 using 5M sodium hydroxide solution (~95 mL) and the mixture stirred until the reaction was complete. The pH was adjusted to 8.3±0.2 by the addition of 5.5M hydrochloric acid solution (~24 mL). The aqueous phase was discarded, further water (200 mL) added and the pH adjusted to <4 by the addition of 5.5M hydrochloric acid solution (~25 mL). The MIBK phase was discarded and the pH of the aqueous phase was adjusted to 7.5 by the addition of 5M sodium hydroxide (~6.5 mL). A seed of mutilin 14-(exo-8-methyl-8-azabicyclo[3.2.1]oct-3-ylsulfanyl)-acetate (50 mg) was added and the mixture stirred until crystallization occurred (typically <30 min). Further 5M sodium hydroxide solution (~12.5 mL) was added over 1 h. The slurry was stirred for 1 h, the product isolated, washed with water (100 mL) and dried under vacuum (40-50° C.) to give the title compound in a yield of 90-95% based on assay.

Step 6a—Purification of Mutilin 14-(exo-8-methyl-8-azabicyclo[3.2.1]oct-3-ylsulfanyl)-acetate Crude product from Step 5a (626.54 g) was suspended in a stirred mixture of ethyl acetate (2.5 L) and filtered, deionised water (2 L). The pH was adjusted from 8.35 to 1.05 by the addition of 2M hydrochloric acid (430 mL) and after stirring for about 15 min the phases were separated. The acidic aqueous phase was washed with further ethyl acetate (650 mL). After separation the aqueous phase was stirred with dichloromethane (1.5 L) and sodium bicarbonate solution (200 g in 2 L deionised water) for 15 min. The phases were separated and the aqueous phase extracted with further dichloromethane (1 L). The combined dichloromethane extracts were concentrated using a Buchi rotary evaporator (bath temperature of 40° C. and Edwards pump) to leave a residue of 266.33 g. This was dissolved in 2-propanol (900 mL) by heating to 60° C. and the solution filtered. The filtrate was heated to reflux and deionised water (1.23 L) added to give a slightly turbid solution at 60° C. On reheating to 62° C. this became clear; the solution was allowed to cool overnight to ambient temperature to give crystalline product. Further filtered deionised water (200 mL) was added slowly to the mixture, which was then cooled to 5° C. and stirred for 1.25 h. The product was filtered off, washed with a chilled 3:2 mixture of water/2-propanol (250 mL) and dried in a dessicator under high vacuum for 64 h, to give title compound 201.5 g (66.5% from pleuromutilin).

Step 6b—Alternative purification of Mutilin 14-(exo-8-methyl-8-azabicyclo[3.2.1]oct-3-ylsulfanyl)-acetate Mutilin 14-(exo-8-methyl-8-azabicyclo[3.2.1]oct-3-ylsulfanyl)-acetate (10.5 g), prepared as in Step 5b, c or d, was heated to 80° C. in isopropyl acetate (41 mL) (a solution is obtained at 55-60° C.) to give a cloudy solution. The solution was filtered (~0.78 g of solids collected) and allowed to cool to 50° C. The solution was then seeded and cooled to 47-48° C. The solution became cloudy and crystallization occurred. The solution was cooled to 0° C. and the temperature was maintained for 2 h. The product was filtered off, washed with (1) chilled isopropyl acetate (5 mL), (2) isopropyl acetate/heptane (10 mL) and (3) heptane (10 mL) and dried (6.72 g, 64%).

Step 6c—Alternative purification of Mutilin 14-(exo-8-methyl-8-azabicyclo[3.2.1]oct-3-ylsulfanyl)-acetate Mutilin 14-(exo-8-methyl-8-azabicyclo[3.2.1]oct-3-ylsulfanyl)-acetate (96.2 g), prepared as in Step 5b, c or d, was heated to 65-70° C. in propan-2-ol (335 mL) until a solution was obtained. The solution was filtered and cooled to 35-38° C. The solution was then seeded and stirred at 35-38° C. for 30 min to allow crystallization to occur. The solution was cooled to −5 to −10° C. over 3 h. The title compound was isolated by filtration, washed successively with heptane/propan-2-ol (2:1) and heptane and dried under to vacuum at 35-40° C. to give 72 g, 75%.

Example 1B

Mutilin 14-(exo-8-methyl-8-azabicyclo[3.2.1]oct-3-ylsulfanyl)-acetate

Step 1—Preparation of crude Mutilin 14-(exo-8-methyl-8-azabicyclo[3.2.1]oct-3-ylsulfanyl)-acetate Tropine-3-mesylate (6.0 kg) and potassium thioacetate (9.4 kg) were heated in a mixture of pyridine (24.0 kg) and water (1.2 kg) at 35-40° C. for 37.75 h. The mixture was cooled to 20-25° C., tert-butyl methyl ether (35.5 kg) added and the mixture stirred for 0.5 h. It was filtered with further tert-butyl methyl ether (18.0 kg) added as washings. Water (50 kg) was added and the phases separated. The aqueous phase was washed with tert-butyl methyl ether (4×14.5 kg) and the combined organic phases washed with saturated sodium chloride solution (14.5 kg). The organic solution was concentrated by distillation, collecting 80 L of distillate, ethanol (35.5 kg) was added and the mixture then cooled to 8° C. Sodium methoxide (2.2 kg) was added and the temperature allowed to rise to 20° C. After about 0.5 h pleuromutilin-22-mesylate (4.3 kg) was added and the temperature adjusted to 24° C.; further pleuromutilin-22-mesylate (typically 0.34 kg) may be added after 0.5 to 1.5 h to complete the reaction. The solution was concentrated by distillation under reduced pressure, collecting 40 L of distillate, and then cooled to 24° C. Dichloromethane (80.0 kg), saturated sodium chloride solution (96.0 kg) and water (15.0 kg) were added. After separation the aqueous phase was washed with dichloromethane (32.0 kg). Water (25.0 kg) was added to the combined organic phases and the pH adjusted to 5.68 by the addition of dilute hydrochloric acid (25 L). After separation the organic phase was washed with water (25.0 kg) and 9% w/w sodium bicarbonate solution (26.4 kg). The organic phase was concentrated by distillation under reduced pressure collecting 50 L of distillate. Ethanol (60.0 kg) was added and the distillation continued collecting a further 55 L of distillate. Water (22.0 kg) was added and the mixture stirred for 4-5 h to allow the product to crystallize. If crystallization was not achieved, the solution was concentrated further collecting 23 L of distillate. It was cooled to 22° C. and water (80.0 kg) and ethyl acetate (72.0 kg) added. After further cooling to 8° C. the pH was adjusted to 1.5 by the addition of dilute hydrochloric acid (20 L). After separation the acidic phase was washed with further ethyl acetate (36.0 kg) which was discarded. Dichloromethane (66.6 kg) was added to the acidic phase and the pH adjusted to 7.26 by the addition of ~10% w/w sodium bicarbonate solution (50.9 kg). The aqueous phase was washed with further dichloromethane (33.3 kg) and the combined dichloromethane solutions were concentrated by distillation under reduced pressure collecting 55 L. Ethanol (58.4 kg) was added and the distillation continued collecting 60 L of distillate. Water (17.0 kg) was added over 5.58 h with crystallization occurring after 5 h; further water (14.0 kg) was added and the mixture stirred at 10-15° C. for 3.5 h. The product was isolated, washed (a mixture of water [5.0 kg] and ethanol [4.0 kg]) and dried to give crude mutilin 14-(exo-8-methyl-8-azabicyclo[3.2.1]oct-3-ylsulfanyl)-acetate (3.1 kg at 74.8% assay).

Step 2—Purification of Mutilin 14-(exo-8-methyl-8-azabicyclo[3.2.1]oct-3-ylsulfanyl)-acetate Crude mutilin 14-(exo-8-methyl-8-azabicyclo[3.2.1]oct-3-ylsulfanyl)-acetate (3.1 kg at 74.8%, 2.3 kg at 100%) was dissolved in ethanol (10.0 kg). Water (11.8 kg) was added over 0.8 h with crystallization occurring after 0.2 h. The mixture was stirred at 12-19° C. for 18 h, the product isolated, washed with a mixture of water (12.0 kg) and ethanol (6.4 kg) and dried under vacuum to give mutilin 14-(exo-8-methyl-8-azabicyclo[3.2.1]oct-3-ylsulfanyl)-acetate (1.6 kg at 96.2%, 1.5 kg at 100%, 10.6% yield from tropine-3-mesylate).

Characterizing Data

The infra-red spectrum, DSC thermogram and XRPD pattern of the crystalline mutilin 14-(exo-8-methyl-8-azabicyclo[3.2.1]oct-3-ylsulfanyl)-acetate were recorded (FIGS. 1 to 3).

(B) Salts

General Method

The acid (approximately 180 mM) was suspended and stirred in ethyl acetate (1300 mL) under nitrogen at 18-20° C. A filtered solution of mutilin 14-(exo-8-methyl-8-azabicyclo[3.2.1]oct-3-ylsulfanyl)-acetate (88.6 g, 171.11 mM) in ethyl acetate (900 mL) was added over 4 h at 18-21° C. The mixture was stirred for a further 19 h at ambient temperature and then cooled to 2-5° C. After 1 h the product was filtered off, washed with chilled ethyl acetate (175 mL), pulled as dry as possible on the funnel and then dried at 45-50° C. under vacuum for 68 h.

Example 1B

Using the General Method described above, succinic acid (21.24 g, 179.86 mM) was suspended and stirred in ethyl acetate (1300 mL) under nitrogen at 18-20° C. A filtered solution of mutilin 14-(exo-8-methyl-8-azabicyclo[3.2.1]oct-3-ylsulfanyl)-acetate (88.6 g, 171.11 mM) in ethyl acetate (900 mL) was added over 4 h at 18-21° C. The mixture was stirred for a further 19 h at ambient temperature and then cooled to 2-5° C. After 1 h the product was filtered off, washed with chilled ethyl acetate (175 mL), pulled as dry as possible on the funnel and then dried at 45-50° C. under vacuum for 68 h to yield the hydrosuccinate salt (103.5 g, 95.1%).

Examples 2B to 4B

The General Method described above was used to prepare the hydrofumarate, hydromaleate and tosylate salts of mutilin 14-(exo-8-methyl-8-azabicyclo[3.2.1]oct-3-ylsulfanyl)-acetate.

Example 5B

Succinic acid (2.42 g, 20.49 mM) was heated in isopropanol (25 mL) to give a homogeneous solution (achieved at 52-54° C.). Mutilin 14-(exo-8-methyl-8-azabicyclo[3.2.1]oct-3-ylsulfanyl)-acetate (14.4 g, 20.08 mM) was similarly dissolved in isopropanol (83 mL) by heating to 48-50° C. This solution was added to the succinic acid solution over 20 min maintaining the temperature at 50-52° C. After stirring for a further 45 min at 55° C. the salt crystallized. The mixture was cooled to 0 to 5° C. over ~1.5 h and stirred for a further 1.5 h. The product was filtered off, washed with chilled isopropanol (15 mL) and air dried to yield the hydrosuccinate salt (11.9 g, 93.26%).
Characterizing Data
The infra-red spectra, DSC thermograms and XRPD patterns of the salts were recorded (FIGS. 4 to 15).

C) Compositions

Example 1C

Step 1—Milling of mutilin 14-(exo-8-methyl-8-azabicyclo[3.2.1]oct-3-ylsulfanyl)-acetate or a pharmaceutically acceptable salt or solvate thereof A 4 inch (10.2 cm) spiral air jet mill operated with a grinding pressure of 30 PSI (207 kPa) was used to obtain the target particle size. The mutilin compound was fed into the mill at a rate of 1 kg/hr.

Step 2—Formulation

Petrolatum was melted to 65° C.±5° C. Appropriately sized particles of the drug substance were uniformly dispersed in the molten petrolatum under high shear (4000 rpm). The dispersion was cooled to 45° C.±5° C. under low shear (1500 rpm). The dispersion was then cooled to 25° C.±5° C. without mixing to give a smooth ointment. The scale of manufacture was 8.5 kg.

Example 2C

Step 1—Milling of mutilin 14-(exo-8-methyl-8-azabicyclo[3.2.1]oct-3-ylsulfanyl)-acetate or a pharmaceutically acceptable salt or solvate thereof An opposed air jet mill operated with a grinding pressure of 10 PSI, and a venturi pressure of 10 PSI was used to obtain the target particle size. The mutilin compound was double passed through the mill at a rate of 10 kg/h.

Step 2—Formulation

Petrolatum was melted to 65-70° C., with countersweep mixing (20 rpm) initiated at 45° C. The molten petrolatum was homogenized and the countersweep mixer was turned off. Appropriately sized particles of the drug substance were uniformly dispersed in the molten petrolatum under high shear (1000 rpm). The counter sweep mixer (20 rpm) was reactivated and the dispersion mixed for thirty minutes. The dispersion was cooled to 50-56° C. with homogenization (1000 rpm) and countersweep mixing (20 rpm). The dispersion was pumped into a holding tank and allowed to cool to 20-30° C. without mixing to give a smooth ointment. The scale of manufacture was 150 kg.

Example 3C

Step 1—Milling of mutilin 14-(exo-8-methyl-8-azabicyclo[3.2.1]oct-3-ylsulfanyl)-acetate or a pharmaceutically acceptable salt or solvate thereof The mutilin compound particle size was reduced to the appropriate size by double passage through a high speed impact mill, fitted with pins and operated at 14,000 rpm. After milling, the drug substance was passed through a 90 μm screen.

Step 2—Formulation

Petrolatum was pre-melted in the drum using an induction drum heater. The molten petrolatum was transferred to the processing vessel, and heating and agitation (30 rpm) were initiated. When the temperature reached 65-70° C., high shear homogenization (3000 rpm) was initiated and the recirculation loop was engaged. After mixing for five minutes, the recirculation loop was closed, and agitation and homogenization were terminated. Homogenization was initiated at lower speed (1500 rpm). Upon vortex formation, appropriately sized particles of the drug were uniformly dispersed in the molten petrolatum. The batch was mixed for 20-30 minutes, with high shear homogenization (3000 rpm), agitation (30 rpm), and with the recirculation loop engaged. The product was then cooled. At 48-50° C., homogenization speed was reduced to 1500 rpm. Remaining product in the recirculation loop was pulled back into the vessel, and the recirculation loop was closed and homogenization stopped. The product was cooled to 34-40° C., and agitation was maintained at 30 rpm. The dispersion was discharged to a conical holding vessel under homogenization and agitation to give a smooth ointment. The scale of manufacture was 250 kg.

The above methods may be used to prepare the following compositions:

|  | Strength (% w/w): | | |
| --- | --- | --- | --- |
|  | 0.5% | 1.0% | 2.0% |
| Drug substance: mutilin 14-(exo-8-methyl-8-azabicyclo[3.2.1]oct-3-ylsulfanyl)-acetate (milled) | 5 g | 10 g | 20 g |
| Ointment base: petrolatum (USP or Ph. Eur.) | qs 1000 g | qs 1000 g | qs 1000 g |

What is claimed is:

1. A method of treating a microbial infection in a mammal, comprising administering topically to said mammal, in need thereof an effective amount of a crystalline mutilin 14-(exo-8-methyl-8-azabicyclo[3.2.1]oct-3-ylsulfanyl)-acetate characterized by at least one of:
   (i) an infra-red spectrum measured by attenuated total reflectance having peaks at 3234, 1735 and 1725 cm$^{-1}$,
   (ii) a differential scanning calorimetry profile having an endotherm with an onset temperature of 125-127° C., and
   (iii) an X-ray powder diffraction pattern having peaks at about 9.6, about 12.8, about 13.9 and about 19.6.

2. The method according to claim 1 wherein the microbial infection is a skin or soft tissue infection.

3. The method according to claim 2 wherein the topical administration of the mutilin is twice daily.

4. The method according to claim 1 wherein the topical administration of the mutilin over a period of 5 to 7 days.

5. A method of treating a microbial infection in a mammal, comprising administering topically to said mammal in need thereof, an effective amount of a crystalline hydrosuccinate salt of mutilin 14-(exo-8-methyl-8-azabicyclo[3.2.1]oct-3-ylsulfanyl)-acetate characterized by at least one of:
   (i) an infra-red spectrum measured by attenuated total reflectance having peaks at 3470, 1731 and 1711 cm$^{-1}$,
   (ii) a differential scanning calorimetry profile having an endotherm with an onset temperature of 168-170° C., and
   (iii) an X-ray powder diffraction pattern having peaks at about 13.4, about 14.4 and about 20.7.

6. The method according to claim 5 wherein the microbial infection is a skin or soft tissue infection.

7. The method according to claim 6 wherein the topical administration of the mutilin is twice daily.

8. The method according to claim 5 wherein the topical administration of the mutilin over a period of 5 to 7 days.

9. A method of treating a microbial infection in a mammal in need thereof, comprising administering topically to said mammal an effective amount of a crystalline mutilin 14-(exo-8-methyl-8-azabicyclo[3.2.1]oct-3-ylsulfanyl)-acetate which is characterized by the following properties:
   (i) an infra-red spectrum measured by ATR (attenuated total reflectance) having peaks at 3234, 1735 and 1725 cm$^{-1}$, and
   (ii) an XRPD (X-ray powder diffraction) pattern having peaks at about 9.6, about 12.8, about 13.9 and about 19.6.

10. The method according to claim 9 wherein the microbial infection is a skin or soft tissue infection.

11. The method according to claim 10 wherein the topical administration of the mutilin is twice daily.

12. The method according to claim 9 wherein the topical administration of the mutilin over a period of 5 to 7 days.

13. A method of treating a microbial infection in a mammal in need thereof, comprising administering topically to said mammal an effective amount of a crystalline mutilin 14-(exo-8-methyl-8-azabicyclo[3.2.1]oct-3-ylsulfanyl)-acetate- which is characterized by one or more of the following properties:
   (i) an infra-red spectrum measured by ATR (attenuated total reflectance) substantially in accordance with FIG. 1;
   (ii) a DSC (differential scanning calorimetry) substantially in accordance with FIG. 2; and
   (iii) an XRPD (X-ray powder diffraction pattern) substantially in accordance with FIG. 3.

14. The method according to claim 13 wherein the microbial infection is a skin or soft tissue infection.

15. The method according to claim 11 wherein the topical administration of the mutilin is twice daily.

16. The method according to claim 13 wherein the topical administration of the mutilin over a period of 5 to 7 days.

17. A method of treating acne in a human, comprising administering topically to said human in need thereof, an effective amount of a crystalline mutilin 14-(exo-8-methyl-8-azabicyclo[3.2.1]oct-3-ylsulfanyl)-acetate characterized by at least one of:
   (i) an infra-red spectrum measured by attenuated total reflectance having peaks at 3234, 1735 and 1725 cm$^{-1}$,
   (ii) a differential scanning calorimetry profile having an endotherm with an onset temperature of 125-127° C., and
   (iii) an X-ray powder diffraction pattern having peaks at about 9.6, about 12.8, about 13.9 and about 19.6.

18. A method of treating a microbial infection in a mammal, comprising administering topically to said mammal, in need thereof an effective amount of a crystalline hydrosuccinate salt of mutilin 14-(exo-8-methyl-8-azabicyclo[3.2.1]oct-3-ylsulfanyl)-acetate characterized by at least one or more of the following properties:
   (i) an infra-red spectrum measured by ATR (attenuated total reflectance) having peaks at 3470, 1731 and 1711 cm$^{-1}$,
   (ii) a DSC (differential scanning calorimetry) profile having an endotherm with an onset temperature of 168-170° C,
   (iii) an XRPD (X-ray powder diffraction) pattern having peaks at about 13.4, about 14.4 and about 20.7 2-theta.

19. The method according to claim 18 wherein the crystalline hydrosuccinate salt of the mutilin are particles incorporated into an ointment.

20. The method according to claim 19 wherein the ointment is petrolatum.

21. The method according to claim 19 wherein the $D_{90}$ of the particles in the composition is 15 μm to 25 μm.

22. The method according to claim 1 wherein the crystalline mutilin particles are incorporated into an ointment.

23. The method according to claim 22 wherein the ointment is petrolatum.

24. The method according to claim 22 wherein the $D_{90}$ of the particles in the composition is 15 μm to 25 μm.

* * * * *